United States Patent
Fischer et al.

(10) Patent No.: US 7,262,202 B2
(45) Date of Patent: Aug. 28, 2007

(54) INHIBITORS OF CYCLIN DEPENDENT KINASES AS ANTI-CANCER AGENT

(75) Inventors: Peter Martin Fischer, Angus (GB); Shudong Wang, Angus (GB); Gavin Wood, Fife (GB)

(73) Assignee: Cyclacel Limited, London, England (GB)

( * ) Notice: Subject to any disclaimer, the term of this patent is extended or adjusted under 35 U.S.C. 154(b) by 0 days.

(21) Appl. No.: 10/671,747

(22) Filed: Sep. 24, 2003

(65) Prior Publication Data

US 2004/0132746 A1 Jul. 8, 2004

Related U.S. Application Data

(63) Continuation of application No. PCT/GB02/01445, filed on Mar. 26, 2002.

(30) Foreign Application Priority Data

Mar. 29, 2001 (GB) ................... 0107901.1

(51) Int. Cl.
*C07D 403/04* (2006.01)
*A61K 31/4025* (2006.01)
*C07D 207/36* (2006.01)

(52) U.S. Cl. ................. 514/275; 544/331; 548/537

(58) Field of Classification Search ............. 544/331; 514/275

See application file for complete search history.

(56) References Cited

U.S. PATENT DOCUMENTS

2003/0092714 A1* 5/2003 Cao et al. ................. 514/242
2003/0203926 A1* 10/2003 Kois et al. ................. 514/275

FOREIGN PATENT DOCUMENTS

| EP | 0 233 461 A2 | 8/1987 |
| EP | 0 588 762 A1 | 8/1992 |
| WO | WO95/09852 A1 | 4/1995 |
| WO | WO97/19065 A1 | 5/1997 |
| WO | WO 00/39101 A1 | 7/2000 |
| WO | WO 02/46171 A2 | 6/2002 |

OTHER PUBLICATIONS

Torley et al., CAPLUS Abstract 18:112478 (RN 112722-32-4), 1988.*
Simone, Oncology: Introduction, Cecil Textbook of Medicine, 20th Edition, vol. 1, pp. 1004-1010, 1996.*
Blain et al., Differential Interaction of thet Cyclin-dependent Kinase (Cdk) inhibitor p27 with Cyclin-A-Cdk2 and Cyclin D2-Cdk4, The Journal of Biological Chemistry, vol. 272, No. 41, pp. 25863-25872, 1997.*
LuValle et al., Cell Cycle Control in Growth Plate Chondrocytes, Frontiers in Bioscience 5, d493-503, May 2000.*

* cited by examiner

*Primary Examiner*—Deepak Rao
(74) *Attorney, Agent, or Firm*—Lahive & Cockfield, LLP; Giulio A. DeConti, Jr.; Cynthia L. Kanik

(57) ABSTRACT

The present invention relates to 2-substituted 4-heteroaryl-pyrimidines, their preparation, pharmaceutical compositions containing them and their use as inhibitors of cyclin-dependent kinases (CDKs) and hence their use in the treatment of proliferative disorders such as cancer, leukaemia, psoriasis and the like.

41 Claims, 4 Drawing Sheets

| No. | Structure |
|---|---|
| 1 | 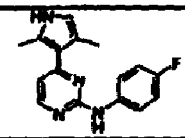 |
| 2 | 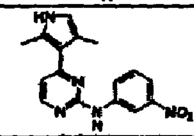 |
| 3 | 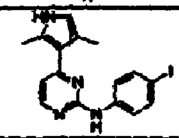 |
| 4 | 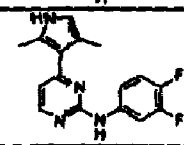 |
| 5 | 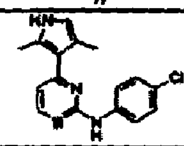 |
| 6 | 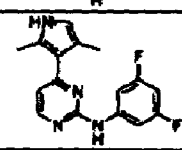 |
| 7 | 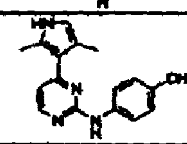 |
| 8 | 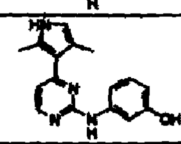 |
| 9 | 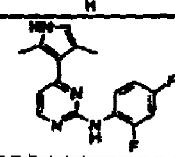 |
| 10 | 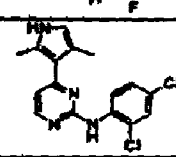 |
| 11 | 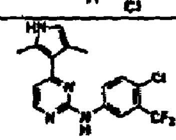 |

Fig. 1 (continued)

| 12 | |
| --- | --- |
| 13 | |
| 14 | |
| 15 | |
| 16 | |
| 17 | |
| 31 | |
| 32 | |
| 33 | |
| 34 | |
| 35 | |

INHIBITORS OF CYCLIN DEPENDENT KINASES AS ANTI-CANCER AGENT

RELATED APPLICATIONS

This application is a continuation of PCT/GB02/01445, which was filed on Mar. 26, 2002, and which claims priority to GB 0107901.1, which was filed on Mar. 29, 2001. The entire contents of each of these applications are hereby incorporated herein by reference.

The present invention relates to 2-substituted 4-heteroaryl-pyrimidines, their preparation, pharmaceutical compositions containing them, and their use in the treatment of proliferative disorders such as cancer, leukemia, psoriasis and the like.

INTRODUCTION AND SUMMARY OF THE PRIOR ART

Certain 4,5,6-substituted-N-(substituted-phenyl)-2-pyrimidineamines having anti-asthmatic properties are disclosed in EP-A-233,461. Certain 4-heteroaryl-N-(3-substituted-phenyl)-2-pyridineamines possessing anti-proliferative properties and inhibiting protein kinases C, epidermal growth factor receptor-associated tyrosine protein kinase (EGF-R-TPK), as well as CDK1/cyclin B have been disclosed in WO95/09847 wherein the exemplified heteroaryl are pyridyl and indolyl.

J. Med. Chem. (1993) Vol. 36, pages 2716–2725, Paul, R. et al: discloses a further class of phenyl amino-pyrimidines possessing anti-inflammatory activity. These compounds include unsubstituted pyrrol groups, mono-substituted 2-thienyl groups and dimethyl-3-furyl groups at the 4-position of the pyrimidine ring.

It is an aim of the present invention to provide a further class of N-phenyl-2-pyrimidine anti-proliferative compounds. The compounds of the present invention have surprisingly been found to not to be inhibitors of protein kinase C. As discussed hereinafter, their activity may be demonstrated by inhibition of cell proliferation in cell lines and/or inhibition of cyclin dependent kinase enzymes.

SUMMARY OF THE INVENTION

The first aspect of the present invention relates to compounds of general formula I:

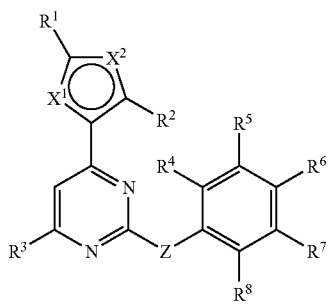

I wherein:
one of $X^1$ and $X^2$ is $NR^{10}$ and the other of $X^1$ and $X^2$ is $CR^9$;
Z is NH, NHCO, NHSO$_2$, NHCH$_2$, CH$_2$, CH$_2$CH$_2$, or CH=CH;

$R^1$, $R^2$, $R^3$, $R^9$ and $R^{10}$ are independently H, alkyl, aryl, aralkyl, heterocycle, halogeno, NO$_2$, CN, OH, alkoxy, aryloxy, (R''')$_n$NH$_2$, (R''')$_n$NH—R', (R''')$_n$N—(R')(R''), NH-aryl, N-(aryl)$_2$, COOH, COO—R', COO-aryl, CONH$_2$, CONH—R', CON—(R')(R''), CONH-aryl, CON-(aryl)$_2$, SO$_3$H, SO$_2$NH$_2$, CF$_3$, CO—R', or CO-aryl, wherein alkyl, aryl, aralkyl and heterocycle groups may be further substituted with one or more groups selected from halogen, NO$_2$, CN, OH, O-methyl, NH$_2$, COOH, CONH$_2$ and CF$_3$;

$R^4$, $R^5$, $R^6$, $R^7$, and $R^8$ are independently from each other H, substituted or unsubstituted lower alkyl, halogeno, NO$_2$, CN, OH, substituted or unsubstituted alkoxy, NH$_2$, NH—R', N—(R')(R''), COOH, COO—R', CONH$_2$, CONH—R', CON—(R')(R''), SO$_3$H, SO$_2$NH$_2$, or CF$_3$;

wherein R'R'' and R''' are each independently alkyl groups that may be the same or different and n is 0 or 1;

with the proviso that when $R^1$ and $R^2$ are H, $X^1$ is NH, $X^2$ is CH, and $R^3$ is H, the phenyl group is not
unsubstituted,
4-ethyl,
3-methyl,
3-(1,1,2,2-tetrafluoroethoxy),
3,4,5-trimethoxy,
when the other groups $R^4$–$R^8$ are H;

and pharmaceutically acceptable salts thereof.

DESCRIPTION OF THE PREFERRED EMBODIMENTS

As used herein the term "alkyl" includes both straight chain and branched alkyl groups having from 1 to 8 carbon atoms, e.g. methyl, ethyl propyl, isopropyl, butyl, isobutyl, tert-butyl, pentyl, hexyl etc and the term "lower alkyl" is similarly used for groups having from 1 to 4 carbon atoms.

The term "aryl" is used to include groups having from 6 to 10 carbon atoms, e.g. phenyl, naphthyl etc.

The term "aralkyl" is used as a conjunction of the terms alkyl and aryl as given above.

Preferred compounds of formula I are those bearing a mono-, di- or trisubstituted pyrrol radical, attached to the pyrimidine ring through one of the ring carbon atoms. Preferably, the pyrrol radical is a pyrrol-3-yl group (i.e. $X^1$ is $CR^9$ and $X^2$ is $NR^{10}$, preferably NH) and is di- or tri-substituted.

The pyrrol group may be substituted by $R^1$, $R^2$, $R^9$ and $R^{10}$. Preferably, $R^1$, $R^2$ and where appropriate $R^9$ and $R^{10}$ are independently H, alkyl, aryl, aralkyl, heterocycle, halogeno, NO$_2$, CN, OH, alkoxy, aryloxy, (R''')nNH$_2$, (R''')$_n$NH—R', (R''')nN—(R')(R''), NH-aryl, N-(aryl)$_2$, COOH, COO—R', COO-aryl, CONH$_2$, CONH—R', CON—(R')(R''), CONH-aryl, CON-(aryl)$_2$, SO$_3$H, SO$_2$NH$_2$, CF$_3$, CO—R', or CO-aryl, wherein alkyl, aryl, aralkyl and heterocycle groups may be further substituted with one or more groups selected from halogeno, NO$_2$, CN, OH, O-methyl, NH$_2$, COOH, CONH$_2$ and CF$_3$. Most preferably $R^{10}$ is H.

More preferably, $R^1$, $R^2$ and $R^9$ are each independently selected from H, halogeno, NO$_2$, CN, (R''')nN—(R')(R''), CONH$_2$, a $C_{1-4}$ alkyl group and a heterocyclic group. Preferably, at least one, more preferably at least two or three of $R^1$, $R^2$ and $R^9$ are not hydrogen.

Preferably, $R^1$ is H, CN, halogeno, nitro, alkylamino or a heterocyclic group. When $R^1$ is halogeno, it is preferably selected from chloro or bromo. When $R^1$ is alkylamino, it is preferably diethylaminomethyl or dimethylaminomethyl When R¹ is a heterocyclic group it is preferably morpholin-4-ylmethyl or 4-methyl-piperazin-1-ylmethyl. Most preferably, R¹ is H or CN.

Even more preferably, when R¹ is as preferably described, R² and R⁹ are both lower alkyl, preferably methyl.

The group Z is preferably NH, NHSO₂ or NHCH₂, most preferably NH.

The phenyl substituents R⁴–R⁸ are each independently selected from H, halogeno, nitro, amino, aminoalkyl, hydroxy, alkoxy, carbamoyl, sulfamyl, CN, N(R')(R"), $C_{1-4}$ alkyl and substituted $C_{1-4}$ alkyl.

More preferably, R⁴, R⁵, R⁶, R⁷, and R⁸ are independently from each other H, unsubstituted lower alkyl, halogeno, NO₂, CN, OH, N—(R')(R"), or CF₃;

wherein R' R" and R'" are each independently alkyl groups that may be the same or different and n is 0 or 1;

Even more preferably, R⁴ to R⁸ are selected independently from H, F, NH₂, NO₂, OH, Cl, Br, I, CN, CH₂OH, CF₃ and dimethylamino. Within the preferences for R⁴ to R⁸, R⁴ and R⁸ are most preferably hydrogen.

Thus, particularly preferred embodiments include 2-[N-(phenyl)]-4-(2,4-dimethylpyrrol-3-yl)pyrimidineamines in which the phenyl group is 2-, 3- or 4-substituted by at least one of H, F, NH₂, NO₂, OH, Cl, Br, I, CN, CH₂OH, CF₃ or OMe.

Within this particular embodiment, the phenyl group is preferably mono-substituted by F, NH₂, NO₂, OH, Cl, Br, I, CH₂OH, CN, CF₃ or OMe at any of the 2, 3 or 4-positions, or di-substituted by 2,4-difluoro, 3,5-difluoro, 3,4-difluoro, 2,4-dichloro, 3,5-dichloro, 3,4-dichloro or 4-chloro-3-trifluoromethyl.

Further particularly preferred embodiments include 2-[N-(phenyl)]-4-(3,5-dimethyl-1H-pyrrole-2-carbonitrile)pyrimidineamines in which the phenyl group is 2-, 3- or 4-substituted by at least one of F, NH(CH₃)₂, NO₂, OH, Cl, Br, I or CF₃.

Within this particular embodiment, the phenyl group is preferably mono-substituted by F, NH(CH₃)₂, NO₂, OH, I or CF₃ at any of the 3 or 4-positions, or di-substituted by 4-methyl-3-nitro, 3-iodo-4-methyl, 4-chloro-3-methyl, 3-hydroxy-4-methyl, 4-fluoro-3-methyl or 4-methyl-3-fluoro.

Further more particularly preferable embodiments include;

2-[N-(phenyl)]-4-(2,4-Dimethyl-5-nitro-1H-pyrrol-3-yl)-pyrimidinamines wherein the phenyl group is preferably mono-substituted by F, NH(CH₃)₂, NO₂, OH, I at the 4-position, preferably by a fluoro or NH(CH₃)₂ group.

2-[N-(phenyl)]-4-(2,4-dimethyl-5-halogeno-1H-pyrrol-3-yl)-pyrimidinamines wherein the phenyl group is preferably mono-substituted by F, NH(CH₃)₂, NO₂, OH, I or CF₃ at the 3 or 4-positions, preferably by a 4-fluoro or 3-nitro group, the halogeno group preferably being chloro or bromo.

2-[N-(phenyl)]-4-(2,4-dimethyl-5-dialkylaminoalkyl-1H-pyrrol-3-yl)-pyrimidinamines wherein the phenyl group is preferably mono-substituted by F, NH(CH₃)₂, NO₂, OH, I or CF₃ at the 4-position, preferably by fluoro, the dialkylaminoalkyl group preferably being diethylaminomethyl or dimethylaminomethyl.

2-[N-(phenyl)]-4-(2,4-dimethyl-5-(heterocycle)-1H-pyrrol-3-yl)-pyrimidinamines wherein the phenyl group is preferably mono-substituted by F, NH(CH₃)₂, NO₂, OH, I or CF₃ at the 4-position, preferably by fluoro, the heterocycle group preferably being 5-morpholin-4-yl-methyl or 4-methyl-piperazin-1-ylmethyl.

Most preferably, the compounds of the present invention are selected from;

[4-(2,4-Dimethyl-1H-pyrrol-3-yl)-pyrimidin-2-yl]-(4-fluoro-phenyl)-amine

[4-(2,4-Dimethyl-1H-pyrrol-3-yl)-pyrimidin-2-yl]-(3-nitro-phenyl)-amine

[4-(2,4-Dimethyl-1H-pyrrol-3-yl)-pyrimidin-2-yl]-(4-iodo-phenyl)-amine (3,4-Difluoro-phenyl)-[4-(2,4-dimethyl-1H-pyrrol-3-yl)-pyrimidin-2-yl]-amine (4-Chloro-phenyl)-[4-(2,4-dimethyl-1H-pyrrol-3-yl)-pyrimidin-2-yl]-amine (3,5-Difluoro-phenyl)-[4-(2,4-dimethyl-1H-pyrrol-3-yl)-pyrimidin-2-yl]-amine 4-[4-(2,4-Dimethyl-1H-pyrrol-3-yl)-pyrimidin-2-ylamino]-phenol 3-[4-(2,4-Dimethyl-1H-pyrrol-3-yl)-pyrimidin-2-ylamino]-phenol (2,4-Difluoro-phenyl)-[4-(2,4-dimethyl-1H-pyrrol-3-yl)-pyrimidin-2-yl]-amine (2,4-Dichloro-phenyl)-[4-(2,4-dimethyl-1H-pyrrol-3-yl)-pyrimidin-2-yl]-amine (4-Chloro-3-trifluoromethyl-phenyl)-[4-(2,4-dimethyl-1H-pyrrol-3-yl)-pyrimidin-2-yl]-amine

[4-(2,4-Dimethyl-1H-pyrrol-3-yl)-pyrimidin-2-yl]-(4-trifluoromethyl-phenyl)-amine

[4-(2,4-Dimethyl-1H-pyrrol-3-yl)-pyrimidin-2-yl]-(3-trifluoromethyl-phenyl)-amine (3-Chloro-phenyl)-[4-(2,4-dimethyl-1H-pyrrol-3-yl)-pyrimidin-2-yl]-amine N-[4-(2,4-Dimethyl-1H-pyrrol-3-yl)-pyrimidin-2-yl]-N',N'-dimethyl-benzene-1,4-diamine (3-Chloro-4-iodo-phenyl)-[4-(2,4-dimethyl-1H-pyrrol-3-yl)-pyrimidin-2-yl]-amine

[4-(2,4-Dimethyl-1H-pyrrol-3-yl)-pyrimidin-2-yl]-(3-fluoro-4-iodo-phenyl)-amine 3,5-Dimethyl-4-[2-(3-nitro-phenylamino)-pyrimidin-4-yl]-1H-pyrrole-2-carbonitrile 4-[2-(4-Fluoro-phenylamino)-pyrimidin-4-yl]-3,5-dimethyl-1H-pyrrole-2-carbonitrile 4-[2-(4-Hydroxy-phenylamino)-pyrimidin-4-yl]-3,5-dimethyl-1H-pyrrole-2-carbonitrile 3,5-Dimethyl-4-[2-(4-trifluoromethyl-phenylamino)-pyrimidin-4-yl]-1H-pyrrole-2-carbonitrile 4-[2-(4-Iodo-phenylamino)-pyrimidin-4-yl]-3,5-dimethyl-1H-pyrrole-2-carbonitrile 4-[2-(3-Hydroxy-phenylamino)-pyrimidin-4-yl]-3,5-dimethyl-1H-pyrrole-2-carbonitrile 3,5-Dimethyl-4-[2-(4-methyl-3-nitro-phenylamino)-pyrimidin-4-yl]-1H-pyrrole-2-carbonitrile 4-[2-(3-Iodo-4-methyl-phenylamino)-pyrimidin-4-yl]-3,5-dimethyl-1H-pyrrole-2-carbonitrile 4-[2-(4-Chloro-3-methyl-phenylamino)-pyrimidin-4-yl]-3,5-dimethyl-1H-pyrrole-2-carbonitrile 4-[2-(3-Hydroxy-4-methyl-phenylamino)-pyrimidin-4-yl]-3,5-dimethyl-1H-pyrrole-2-carbonitrile 4-[2-(4-Fluoro-3-methyl-phenylamino)-pyrimidin-4-yl]-3,5-dimethyl-1H-pyrrole-2-carbonitrile 4-[2-(3-Fluoro-4-methyl-phenylamino)-pyrimidin-4-yl]-3,5-dimethyl-1H-pyrrole-2-carbonitrile 4-[2-(4-Dimethylamino-phenylamino)-pyrimidin-4-yl]-3,5-dimethyl-1H-pyrrole-2-carbonitrile 4-[2-(4-Fluoro-phenylamino)-pyrimidin-4-yl]-3,5-dimethyl-1H-pyrrole-2-carboxylic acid amide

[4-(3,5-Dimethyl-1H-pyrrol-2-yl)-pyrimidin-2-yl]-(4-fluoro-phenyl)-amine
(4-Fluoro-phenyl)-[4-(1,2,4-trimethyl-1H-pyrrol-3-yl)-pyrimidin-2-yl]-amine
[4-(2,4-Dimethyl-5-nitro-1H-pyrrol-3-yl)-pyrimidin-2-yl]-(4-fluoro-phenyl)-amine
N-[4-(2,4-Dimethyl-5-nitro-1H-pyrrol-3-yl)-pyrimidin-2-yl]-N',N'-dimethyl-benzene-1,4-diamine
[4-(5-Amino-2,4-dimethyl-1H-pyrrol-3-yl)-pyrimidin-2-yl]-(4-fluoro-phenyl)-amine
[4-(5-Bromo-2,4-dimethyl-1H-pyrrol-3-yl)-pyrimidin-2-yl]-(4-fluoro-phenyl)-amine
[4-(5-Bromo-2,4-dimethyl-1H-pyrrol-3-yl)-pyrimidin-2-yl]-(3-nitro-phenyl)-amine
[4-(5-Chloro-2,4-dimethyl-1H-pyrrol-3-yl)-pyrimidin-2-yl]-(4-fluoro-phenyl)-amine
[4-(5-Diethylaminomethyl-2,4-dimethyl-1H-pyrrol-3-yl)-pyrimidin-2-yl]-(4-fluoro-phenyl)-amine
[4-(5-Dimethylaminomethyl-2,4-dimethyl-1H-pyrrol-3-yl)-pyrimidin-2-yl]-(4-fluoro-phenyl)-amin
[4-(2,4-Dimethyl-5-morpholin-4-ylmethyl-1H-pyrrol-3-yl)-pyrimidin-2-yl]-(4-fluoro-pheny
{4-[2,4-Dimethyl-5-(4-methyl-piperazin-1-ylmethyl)-1H-pyrrol-3-yl]-pyrimidin-2-yl}-(4-fluoro-phenyl)-amine The structures of the above-mentioned compounds are illustrated in FIG. 1.

Particularly preferred compounds observed are those to be CDK inhibitors having $IC_{50}$ for cdk2/cyclinE of less than 5 µM (±0.05), including;
[4-(2,4-Dimethyl-1H-pyrrol-3-yl)-pyrimidin-2-yl]-(4-fluoro-phenyl)-amine
[4-(2,4-Dimethyl-1H-pyrrol-3-yl)-pyrimidin-2-yl]-(3-nitro-phenyl)-amine
[4-(2,4-Dimethyl-1H-pyrrol-3-yl)-pyrimidin-2-yl]-(4-iodo-phenyl)-amine
(3,4-Difluoro-phenyl)-[4-(2,4-dimethyl-1H-pyrrol-3-yl)-pyrimidin-2-yl]-amine
(4-Chloro-phenyl)-[4-(2,4-dimethyl-1H-pyrrol-3-yl)-pyrimidin-2-yl]-amine
(3,5-Difluoro-phenyl)-[4-(2,4-dimethyl-1H-pyrrol-3-yl)-pyrimidin-2-yl]-amine
4-[4-(2,4-Dimethyl-1H-pyrrol-3-yl)-pyrimidin-2-ylamino]-phenol
3-[4-(2,4-Dimethyl-1H-pyrrol-3-yl)-pyrimidin-2-ylamino]-phenol
[4-(2,4-Dimethyl-1H-pyrrol-3-yl)-pyrimidin-2-yl]-(4-trifluoromethyl-phenyl)-amine
(3-Chloro-4-iodo-phenyl)-[4-(2,4-dimethyl-1H-pyrrol-3-yl)-pyrimidin-2-yl]-amine
[4-(2,4-Dimethyl-1H-pyrrol-3-yl)-pyrimidin-2-yl]-(3-fluoro-4-iodo-phenyl)-amine
3,5-Dimethyl-4-[2-(3-nitro-phenylamino)-pyrimidin-4-yl]-1H-pyrrole-2-carbonitrile
4-[2-(4-Fluoro-phenylamino)-pyrimidin-4-yl]-3,5-dimethyl-1H-pyrrole-2-carbonitrile
4-[2-(4-Hydroxy-phenylamino)-pyrimidin-4-yl]-3,5-dimethyl-1H-pyrrole-2-carbonitrile
3,5-Dimethyl-4-[2-(4-trifluoromethyl-phenylamino)-pyrimidin-4-yl]-1H-pyrrole-2-carbonitrile
4-[2-(4-Iodo-phenylamino)-pyrimidin-4-yl]-3,5-dimethyl-1H-pyrrole-2-carbonitrile
4-[2-(3-Hydroxy-phenylamino)-pyrimidin-4-yl]-3,5-dimethyl-1H-pyrrole-2-carbonitrile
3,5-Dimethyl-4-[2-(4-methyl-3-nitro-phenylamino)-pyrimidin-4-yl]-1H-pyrrole-2-carbonitrile
4-[2-(3-Iodo-4-methyl-phenylamino)-pyrimidin-4-yl]-3,5-dimethyl-1H-pyrrole-2-carbonitrile
4-[2-(4-Chloro-3-methyl-phenylamino)-pyrimidin-4-yl]-3,5-dimethyl-1H-pyrrole-2-carbonitrile
4-[2-(3-Hydroxy-4-methyl-phenylamino)-pyrimidin-4-yl]-3,5-dimethyl-1H-pyrrole-2-carbonitrile
4-[2-(4-Fluoro-3-methyl-phenylamino)-pyrimidin-4-yl]-3,5-dimethyl-1H-pyrrole-2-carbonitrile
4-[2-(3-Fluoro-4-methyl-phenylamino)-pyrimidin-4-yl]-3,5-dimethyl-1H-pyrrole-2-carbonitrile
4-[2-(4-Dimethylamino-phenylamino)-pyrimidin-4-yl]-3,5-dimethyl-1H-pyrrole-2-carbonitrile
4-[2-(4-Fluoro-phenylamino)-pyrimidin-4-yl]-3,5-dimethyl-1H-pyrrole-2-carboxylic acid amide
(4-Fluoro-phenyl)-[4-(1,2,4-trimethyl-1H-pyrrol-3-yl)-pyrimidin-2-yl]-amine
[4-(2,4-Dimethyl-5-nitro-1H-pyrrol-3-yl)-pyrimidin-2-yl]-(4-fluoro-phenyl)-amine
N-[4-(2,4-Dimethyl-5-nitro-1H-pyrrol-3-yl)-pyrimidin-2-yl]-N',N'-dimethyl-benzene-1,4-diamine
[4-(5-Bromo-2,4-dimethyl-1H-pyrrol-3-yl)-pyrimidin-2-yl]-(4-fluoro-phenyl)-amine
[4-(5-Bromo-2,4-dimethyl-1H-pyrrol-3-yl)-pyrimidin-2-yl]-(3-nitro-phenyl)-amine
[4-(5-Chloro-2,4-dimethyl-1H-pyrrol-3-yl)-pyrimidin-2-yl]-(4-fluoro-phenyl)-amine
[4-(5-Diethylaminomethyl-2,4-dimethyl-1H-pyrrol-3-yl)-pyrimidin-2-yl]-(4-fluoro-phenyl)-amine
[4-(5-Dimethylaminomethyl-2,4-dimethyl-1H-pyrrol-3-yl)-pyrimidin-2-yl]-(4-fluoro-phenyl)-amin
[4-(2,4-Dimethyl-5-morpholin-4-ylmethyl-1H-pyrrol-3-yl)-pyrimidin-2-yl]-(4-fluoro-pheny and
{4-[2,4-Dimethyl-5-(4-methyl-piperazin-1-ylmethyl)-1H-pyrrol-3-yl]-pyrimidin-2-yl}-(4-fluoro-phenyl)-amine.

Of these compounds, more preferred are those to be CDK inhibitors having $IC_{50}$ for cdk2/cyclinE of less than 1 µM (±0.05), including;
[4-(2,4-Dimethyl-1H-pyrrol-3-yl)-pyrimidin-2-yl]-(4-fluoro-phenyl)-amine
[4-(2,4-Dimethyl-1H-pyrrol-3-yl)-pyrimidin-2-yl]-(3-nitro-phenyl)-amine
[4-(2,4-Dimethyl-1H-pyrrol-3-yl)-pyrimidin-2-yl]-(4-iodo-phenyl)-amine
[4-(2,4-Dimethyl-1H-pyrrol-3-yl)-pyrimidin-2-yl]-(4-trifluoromethyl-phenyl)-amine
3,5-Dimethyl-4-[2-(3-nitro-phenylamino)-pyrimidin-4-yl]-1H-pyrrole-2-carbonitrile
4-[2-(4-Fluoro-phenylamino)-pyrimidin-4-yl]-3,5-dimethyl-1H-pyrrole-2-carbonitrile
4-[2-(4-Hydroxy-phenylamino)-pyrimidin-4-yl]-3,5-dimethyl-1H-pyrrole-2-carbonitrile
3,5-Dimethyl-4-[2-(4-trifluoromethyl-phenylamino)-pyrimidin-4-yl]-1H-pyrrole-2-carbonitrile
4-[2-(4-Iodo-phenylamino)-pyrimidin-4-yl]-3,5-dimethyl-1H-pyrrole-2-carbonitrile
4-[2-(3-Hydroxy-phenylamino)-pyrimidin-4-yl]-3,5-dimethyl-1H-pyrrole-2-carbonitrile
3,5-Dimethyl-4-[2-(4-methyl-3-nitro-phenylamino)-pyrimidin-4-yl]-1H-pyrrole-2-carbonitrile
4-[2-(3-Iodo-4-methyl-phenylamino)-pyrimidin-4-yl]-3,5-dimethyl-1H-pyrrole-2-carbonitrile
4-[2-(4-Chloro-3-methyl-phenylamino)-pyrimidin-4-yl]-3,5-dimethyl-1H-pyrrole-2-carbonitrile
4-[2-(3-Hydroxy-4-methyl-phenylamino)-pyrimidin-4-yl]-3,5-dimethyl-1H-pyrrole-2-carbonitrile
4-[2-(4-Fluoro-3-methyl-phenylamino)-pyrimidin-4-yl]-3,5-dimethyl-1H-pyrrole-2-carbonitrile
4-[2-(3-Fluoro-4-methyl-phenylamino)-pyrimidin-4-yl]-3,5-dimethyl-1H-pyrrole-2-carbonitrile 4-[2-(4-Dimethylamino-phenylamino)-pyrimidin-4-yl]-3,5-dimethyl-1H-pyrrole-2-carbonitrile
4-[2-(4-Fluoro-phenylamino)-pyrimidin-4-yl]-3,5-dimethyl-1H-pyrrole-2-carboxylic acid amide
[4-(2,4-Dimethyl-5-nitro-1H-pyrrol-3-yl)-pyrimidin-2-yl]-(4-fluoro-phenyl)-amine
N-[4-(2,4-Dimethyl-5-nitro-1H-pyrrol-3-yl)-pyrimidin-2-yl]-N',N'-dimethyl-benzene-1,4-diamine
[4-(5-Bromo-2,4-dimethyl-1H-pyrrol-3-yl)-pyrimidin-2-yl]-(4-fluoro-phenyl)-amine
[4-(5-Bromo-2,4-dimethyl-1H-pyrrol-3-yl)-pyrimidin-2-yl]-(3-nitro-phenyl)-amine
[4-(5-Chloro-2,4-dimethyl-1H-pyrrol-3-yl)-pyrimidin-2-yl]-(4-fluoro-phenyl)-amine
[4-(5-Diethylaminomethyl-2,4-dimethyl-1H-pyrrol-3-yl)-pyrimidin-2-yl]-(4-fluoro-phenyl)-amine
[4-(5-Dimethylaminomethyl-2,4-dimethyl-1H-pyrrol-3-yl)-pyrimidin-2-yl]-(4-fluoro-phenyl)-amine, and
[4-(2,4-Dimethyl-5-morpholin-4-ylmethyl-1H-pyrrol-3-yl)-pyrimidin-2-yl]-(4-fluoro-phenyl)-amine.

Of these, even more preferred are compounds are those having IC$_{50}$ for cdk2/cyclinE of less than 0.5 μM (±0.05), being;
[4-(2,4-Dimethyl-1H-pyrrol-3-yl)-pyrimidin-2-yl]-(3-nitro-phenyl)-amine
[4-(2,4-Dimethyl-1H-pyrrol-3-yl)-pyrimidin-2-yl]-(4-iodo-phenyl)-amine
3,5-Dimethyl-4-[2-(3-nitro-phenylamino)-pyrimidin-4-yl]-1H-pyrrole-2-carbonitrile
4-[2-(4-Fluoro-phenylamino)-pyrimidin-4-yl]-3,5-dimethyl-1H-pyrrole-2-carbonitrile
4-[2-(4-Hydroxy-phenylamino)-pyrimidin-4-yl]-3,5-dimethyl-1H-pyrrole-2-carbonitrile
3,5-Dimethyl-4-[2-(4-trifluoromethyl-phenylamino)-pyrimidin-4-yl]-1H-pyrrole-2-carbonitrile
4-[2-(4-Iodo-phenylamino)-pyrimidin-4-yl]-3,5-dimethyl-1H-pyrrole-2-carbonitrile
4-[2-(3-Hydroxy-phenylamino)-pyrimidin-4-yl]-3,5-dimethyl-1H-pyrrole-2-carbonitrile
3,5-Dimethyl-4-[2-(4-methyl-3-nitro-phenylamino)-pyrimidin-4-yl]-1H-pyrrole-2-carbonitrile
4-[2-(3-Hydroxy-4-methyl-phenylamino)-pyrimidin-4-yl]-3,5-dimethyl-1H-pyrrole-2-carbonitrile
4-[2-(4-Fluoro-3-methyl-phenylamino)-pyrimidin-4-yl]-3,5-dimethyl-1H-pyrrole-2-carbonitrile
4-[2-(4-Fluoro-phenylamino)-pyrimidin-4-yl]-3,5-dimethyl-1H-pyrrole-2-carboxylic acid amide
[4-(2,4-Dimethyl-5-nitro-1H-pyrrol-3-yl)-pyrimidin-2-yl]-(4-fluoro-phenyl)-amine
[4-(5-Bromo-2,4-dimethyl-1H-pyrrol-3-yl)-pyrimidin-2-yl]-(3-nitro-phenyl)-amine, and
[4-(5-Dimethylaminomethyl-2,4-dimethyl-1H-pyrrol-3-yl)-pyrimidin-2-yl]-(4-fluoro-phenyl)-amine.

The following compounds are observed to be particularly effective anti-proliferative agents, as demonstrated by cell-based assays:
[4-(2,4-Dimethyl-1H-pyrrol-3-yl)-pyrimidin-2-yl]-(3-nitro-phenyl)-amine
[4-(2,4-Dimethyl-1H-pyrrol-3-yl)-pyrimidin-2-yl]-(4-trifluoromethyl-phenyl)-amine
(3-Chloro-4-iodo-phenyl)-[4-(2,4-dimethyl-1H-pyrrol-3-yl)-pyrimidin-2-yl]-amine
3,5-Dimethyl-4-[2-(3-nitro-phenylamino)-pyrimidin-4-yl]-1H-pyrrole-2-carbonitrile
4-[2-(4-Fluoro-phenylamino)-pyrimidin-4-yl]-3,5-dimethyl-1H-pyrrole-2-carbonitrile
4-[2-(4-Hydroxy-phenylamino)-pyrimidin-4-yl]-3,5-dimethyl-1H-pyrrole-2-carbonitrile
3,5-Dimethyl-4-[2-(4-trifluoromethyl-phenylamino)-pyrimidin-4-yl]-1H-pyrrole-2-carbonitrile
4-[2-(4-Iodo-phenylamino)-pyrimidin-4-yl]-3,5-dimethyl-1H-pyrrole-2-carbonitrile
4-[2-(3-Hydroxy-phenylamino)-pyrimidin-4-yl]-3,5-dimethyl-1H-pyrrole-2-carbonitrile
3,5-Dimethyl-4-[2-(4-methyl-3-nitro-phenylamino)-pyrimidin-4-yl]-1H-pyrrole-2-carbonitrile
4-[2-(3-Iodo-4-methyl-phenylamino)-pyrimidin-4-yl]-3,5-dimethyl-1H-pyrrole-2-carbonitrile
4-[2-(4-Chloro-3-methyl-phenylamino)-pyrimidin-4-yl]-3,5-dimethyl-1H-pyrrole-2-carbonitrile
4-[2-(3-Hydroxy-4-methyl-phenylamino)-pyrimidin-4-yl]-3,5-dimethyl-1H-pyrrole-2-carbonitrile
4-[2-(4-Fluoro-3-methyl-phenylamino)-pyrimidin-4-yl]-3,5-dimethyl-1H-pyrrole-2-carbonitrile
4-[2-(3-Fluoro-4-methyl-phenylamino)-pyrimidin-4-yl]-3,5-dimethyl-1H-pyrrole-2-carbonitrile
4-[2-(4-Dimethylamino-phenylamino)-pyrimidin-4-yl]-3,5-dimethyl-1H-pyrrole-2-carbonitrile
4-[2-(4-Fluoro-phenylamino)-pyrimidin-4-yl]-3,5-dimethyl-1H-pyrrole-2-carboxylic acid amide
(4-Fluoro-phenyl)-[4-(1,2,4-trimethyl-1H-pyrrol-3-yl)-pyrimidin-2-yl]-amine
[4-(2,4-Dimethyl-5-nitro-1H-pyrrol-3-yl)-pyrimidin-2-yl]-(4-fluoro-phenyl)-amine
N-[4-(2,4-Dimethyl-5-nitro-1H-pyrrol-3-yl)-pyrimidin-2-yl]-N',N'-dimethyl-benzene-1,4-diamine
[4-(5-Bromo-2,4-dimethyl-1H-pyrrol-3-yl)-pyrimidin-2-yl]-(3-nitro-phenyl)-amine
[4-(5-Diethylaminomethyl-2,4-dimethyl-1H-pyrrol-3-yl)-pyrimidin-2-yl]-(4-fluoro-phenyl)-amine
[4-(5-Dimethylaminomethyl-2,4-dimethyl-1H-pyrrol-3-yl)-pyrimidin-2-yl]-(4-fluoro-phenyl)-amine, and
{4-[2,4-Dimethyl-5-(4-methyl-piperazin-1-ylmethyl)-1H-pyrrol-3-yl]-pyrimidin-2-yl}-(4-fluoro-phenyl)-amine.

The compounds of formula I have been found to possess anti-proliferative activity and are therefore believed to be of use in the treatment of proliferative disorders such as cancers, leukaemias and other disorders associated with uncontrolled cellular proliferation such as psoriasis and restenosis. As defined herein, an anti-proliferative effect within the scope of the present invention may be demonstrated by the ability to inhibit cell proliferation in an in vitro whole cell assay, for example using any of the cell lines A549, HT29, Saos-2, HeLa or MCF-7, or by showing inhibition of a CDK enzyme (such as CDK2 or CDK4) in an appropriate assay. These assays, including methods for their performance, are described in more detail in Example 3. Using such cell line and enzymes assays it may be determined whether a compound is anti-proliferative in the context of the present invention.

Without wishing to be bound by theory, the compounds of the present invention are believed to exert their anti-proliferative effect in a non-protein kinase C (PKC) dependent manner. Many of the compounds inhibit cyclin-dependent kinase enzymes (CDKs) that have been shown to be involved in cell cycle control. These CDKs include CDK2 and CDK4 and particularly their respective interactions with cyclin E and cyclin D1. These compounds of the present invention are further believed to be advantageous in being selective for CDK enzymes implicated in proliferative diseases. By the term "selective" it is meant that although possible having some inhibitory effect on another enzyme (such as PKC), the compound is preferentially effective against an enzyme implicated in proliferative diseases.

The compounds of the invention may inhibit any of the steps or stages in the cell cycle, for example, formation of the nuclear envelope, exit from the quiescent phase of the cell cycle (G0), G1 progression, chromosome decondensation, nuclear envelope breakdown, START, initiation of DNA replication, progression of DNA replication, termination of DNA replication, centrosome duplication, G2 progression, activation of mitotic or meiotic functions, chromosome condensation, centrosome separation, microtubule nucleation, spindle formation and function, interactions with microtubule motor proteins, chromatid separation and segregation, inactivation of mitotic functions, formation of contractile ring, and cytokinesis functions. In particular, the compounds of the invention may influence certain gene functions such as chromatin binding, formation of replication complexes, replication licensing, phosphorylation or other secondary modification activity, proteolytic degradation, microtubule binding, actin binding, septin binding, microtubule organising centre nucleation activity and binding to components of cell cycle signalling pathways.

A further embodiment of the present invention therefore relates to the use of one or more compounds of formula I in the treatment of proliferative disorders. Preferably, the proliferative disorder is a cancer or leukaemia. The term proliferative disorder is used herein in a broad sense to include any disorder that requires control of the cell cycle, for example cardiovascular disorders such as restenosis and cardiomyopathy, auto-immune disorders such as glomerulonephritis and rheumatoid arthritis, dermatological disorders such as psoriasis, anti-inflammatory, anti-fungal, anti-parasitic disorders such as malaria, emphysema and alopecia. In these disorders, the compounds of the present invention may induce apoptosis or maintain stasis within the desired cells as required.

In a particularly preferred embodiment, the invention relates to the use of one or more compounds of formula I in the treatment of a CDK dependent or sensitive disorder. CDK dependent disorders are associated with an above normal level of activity of one or more CDK enzymes. Such disorders preferably associated with an abnormal level of activity of CDK2 and/or CDK4. A CDK sensitive disorder is a disorder in which an aberration in the CDK level is not the primary cause, but is downstream of the primary metabolic aberration. In such scenarios, CDK2 and/or CDK4 can be said to be part of the sensitive metabolic pathway and CDK inhibitors may therefore be active in treating such disorders. Such disorders are preferably cancer or leukaemic disorders.

A second aspect of the present invention relates to the use of a compound of formula

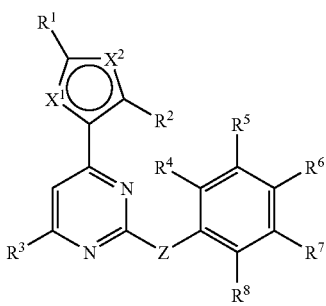

II wherein:
one of $X^1$ and $X^2$ is NH and the other of $X^1$ and $X^2$ is $CR^9$;
Z is NH, NHCO, NHSO$_2$, NHCH$_2$, CH$_2$, CH$_2$CH$_2$, or CH=CH;

$R^1$, $R^2$, $R^3$ and $R^9$ are independently H, alkyl, aryl, aralkyl, heterocycle, halogeno, NO$_2$, CN, OH, alkoxy, aryloxy, NH$_2$, NH—R', N—(R')(R''), NH-aryl, N-(aryl)$_2$, COOH, COO—R', COO-aryl, CONH$_2$, CONH—R', CON—(R') (R''), CONH-aryl, CON-(aryl)$_2$, SO$_3$H, SO$_2$NH$_2$, CF$_3$, CO—R', or CO-aryl, wherein alkyl, aryl, aralkyl and heterocycle groups may be further substituted with one or more groups selected from halogeno, NO$_2$, CN, OH, O-methyl, NH$_2$, COOH, CONH$_2$ and CF$_3$;

$R^4$, $R^5$, $R^6$, $R^7$, and $R^8$ are independently from each other H, substituted or unsubstituted lower alkyl, halogeno, NO$_2$, CN, OH, substituted or unsubstituted alkoxy, NH$_2$, NH—R', N—(R')(R''), COOH, COO—R', CONH$_2$, CONH—R', CON—(R')(R''), SO$_3$H, SO$_2$NH$_2$, or CF$_3$;

wherein R' and R'' are each independently alkyl groups that may be the same or different;

with the proviso that when $R^1$ and $R^2$ are H, $X^1$ is NH, $X^2$ is CH, and $R^3$ is H, the phenyl group is not
3-(1,1,2,2-tetrafluoroethoxy), or
3,4,5-trimethoxy,
when the other groups $R^4$–$R^8$ are H;

and pharmaceutically acceptable salts thereof, in the manufacture of a medicament for use in the treatment of a proliferative disease.

The term "proliferative disorder" has been previously discussed and the same definition applies to the second aspect of the invention.

A further aspect of the present invention relates to the use of the compounds of formula II in the manufacture of a medicament for use in the treatment of antiviral infections. Such viral infections include VZV, HSV type 1 and 2 and HIV. Preferably, the compounds are of use in the treatment of HIV and HIV related disorders.

The preferred embodiments of these further aspects of the invention are identical to those described above in respect of the first aspect.

In a particularly preferred embodiment, the one or more compounds of the invention are administered in combination with one or more other anticancer agents. In such cases, the compounds of the invention may be administered consecutively, simultaneously or sequentially with the one or more other anticancer agents.

As used herein the phrase "manufacture of a medicament" includes the use of a compound of formula I directly as the medicament in addition to its use in a screening programme for further anti-proliferative agents or in any stage of the manufacture of such a medicament.

The compounds of the present invention (first and seconds aspects) can be present as salts or esters, in particular pharmaceutically acceptable salts or esters.

Pharmaceutically acceptable salts of the compounds of the invention (first and seconds aspects) include suitable acid addition or base salts thereof. A review of suitable pharmaceutical salts may be found in Berge et al, J Pharm Sci, 66, 1–19 (1977). Salts are formed, for example with strong inorganic acids such as mineral acids, e.g. sulphuric acid, phosphoric acid or hydrohalic acids; with strong organic carboxylic acids, such as alkanecarboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as (C$_1$–C$_4$)-alkyl- or aryl-sulfonic acids which are unsubstituted or substituted (for example, by a halogen) such as methane- or p-toluene sulfonic acid.

Esters are formed either using organic acids or alcohols/hydroxides, depending on the functional group being esterified. Organic acids include carboxylic acids, such as alkanecarboxylic acids of 1 to 12 carbon atoms which are unsubstituted or substituted (e.g., by halogen), such as acetic acid; with saturated or unsaturated dicarboxylic acid, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as $(C_{1-C4})$-alkyl- or aryl-sulfonic acids which are unsubstituted or substituted (for example, by a halogen) such as methane- or p-toluene sulfonic acid. Suitable hydroxides include inorganic hydroxides, such as sodium hydroxide, potassium hydroxide, calcium hydroxide, aluminium hydroxide. Alcohols include alkanealcohols of 1–12 carbon atoms which may be unsubstituted or substituted, e.g. by a halogen).

In all aspects of the present invention previously discussed, the invention includes, where appropriate all enantiomers and tautomers of compounds of formula I. The man skilled in the art will recognise compounds that possess an optical properties (one or more chiral carbon atoms) or tautomeric characteristics. The corresponding enantiomers and/or tautomers may be isolated/prepared by methods known in the art.

The invention furthermore relates to the compounds of or of use in the present invention (first and seconds aspects) in their various crystalline forms, polymorphic forms and (an)hydrous forms. It is well established within the pharmaceutical industry that chemical compounds may be isolated in any of such forms by slightly varying the method of purification and or isolation form the solvents used in the synthetic preparation of such compounds.

The invention further includes the compounds (first and seconds aspects) of or of use in the present invention in prodrug form. Such prodrugs are generally compounds of formula I wherein one or more appropriate groups have been modified such that the modification may be reversed upon administration to a human or mammalian subject. Such reversion is usually performed by an enzyme naturally present in such subject, though it is possible for a second agent to be administered together with such a prodrug in order to perform the reversion in vivo. Examples of such modifications include ester (for example, any of those described above), wherein the reversion may be carried out be an esterase etc. Other such systems will be well known to those skilled in the art.

The present invention also encompasses pharmaceutical compositions comprising the compounds of the invention (first and seconds aspects). In this regard, and in particular for human therapy, even though the compounds of the present invention (including their pharmaceutically acceptable salts, esters and pharmaceutically acceptable solvates) can be administered alone, they will generally be administered in admixture with a pharmaceutical carrier, excipient or diluent selected with regard to the intended route of administration and standard pharmaceutical practice.

Thus, the present invention also relates to pharmaceutical compositions comprising one or more compounds of formula I or II or pharmaceutically acceptable salts or esters thereof, together with at least one pharmaceutically acceptable excipient, diluent or carrier.

By way of example, in the pharmaceutical compositions of the present invention, the compounds of the invention may be admixed with any suitable binder(s), lubricant(s), suspending agent(s), coating agent(s), and/or solubilising agent(s). Examples of such suitable excipients for the various different forms of pharmaceutical compositions described herein may be found in the "Handbook of Pharmaceutical Excipients, $2^{nd}$ Edition, (1994), Edited by A Wade and P J Weller.

The pharmaceutical compositions of the present invention may be adapted for oral, rectal, vaginal, parenteral, intramuscular, intraperitoneal, intraarterial, intrathecal, intrabronchial, subcutaneous, intradermal, intravenous, nasal, buccal or sublingual routes of administration.

For oral administration, particular use is made of compressed tablets, pills, tablets, gellules, drops, and capsules. Preferably, these compositions contain from 1 to 250 mg and more preferably from 10–100 mg, of active ingredient per dose.

Other forms of administration comprise solutions or emulsions which may be injected intravenously, intraarterially, intrathecally, subcutaneously, intradermally, intraperitoneally or intramuscularly, and which are prepared from sterile or sterilisable solutions. The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. The active ingredient can also be incorporated, at a concentration of between 1 and 10% by weight, into an ointment consisting of a white wax or white soft paraffin base together with such stabilisers and preservatives as may be required.

Injectable forms may contain between 10–1000 mg, preferably between 10–250 mg, of active ingredient per dose.

Compositions may be formulated in unit dosage form, i.e., in the form of discrete portions containing a unit dose, or a multiple or sub-unit of a unit dose.

A person of ordinary skill in the art can easily determine an appropriate dose of one of the instant compositions to administer to a subject without undue experimentation. Typically, a physician will determine the actual dosage which will be most suitable for an individual patient and it will vary with the age, weight and response of the particular patient. The dosages disclosed herein are exemplary of the average case. There can of course be individual instances where higher or lower dosage ranges are merited, and such are within the scope of this invention.

In an exemplary embodiment, one or more doses of 10 to 150 mg/day will be administered to the patient for the treatment of malignancy.

The pharmaceutical compositions of the invention may further comprise one or more additional anticancer agents, for example, existing anticancer drugs available on the market.

Anticancer drugs in general are more effective when used in combination. In particular, combination therapy is desirable in order to avoid an overlap of major toxicities, mechanism of action and resistance mechanism(s). Furthermore, it is also desirable to administer most drugs at their maximum tolerated doses with minimum time intervals between such doses. The major advantages of combining chemotherapeutic drugs are that it may promote additive or possible synergistic effects through biochemical interactions and also may decrease the emergence of resistance in early tumor cells which would have been otherwise responsive to initial chemotherapy with a single agent. An example of the use of biochemical interactions in selecting drug combinations is demonstrated by the administration of leucovorin to increase the binding of an active intracellular metabolite of 5-fluorouracil to its target, thymidylate synthase, thus increasing its cytotoxic effects.

Numerous combinations are used in current treatments of cancer and leukemia. A more extensive review of medical practices may be found in "Oncologic Therapies" edited by E. E. Vokes and H. M. Golomb, published by Springer.

Beneficial combinations may be suggested by studying the growth inhibitory activity of the test compounds with agents known or suspected of being valuable in the treatment of a particular cancer initially or cell lines derived from that cancer. This procedure can also be used to determine the order of administration of the agents, i.e. before, simultaneously, or after delivery. Such scheduling may be a feature of all the cycle acting agents identified herein.

The compounds of this invention (I) can be synthesised, for example, by an adaptation of the Traube synthesis (A. R. Katritzky, I. Taher, Can. J. Chem. 1986, 64, 2087 and references cited therein), i.e. by condensation between 1,3-dicarbonyl compounds 1 or acrylates 2 or 3, and amidine 4, as shown in Scheme 1.

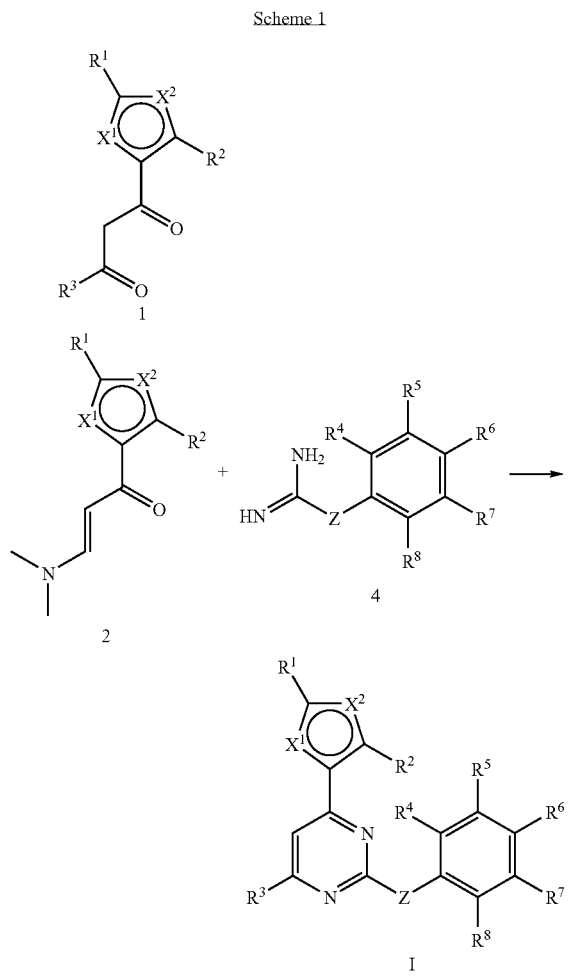

-continued

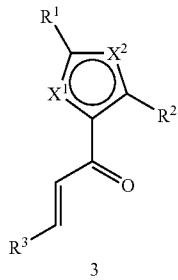

3

The dicarbonyl compounds I in turn can be prepared by many methods known in the art (J. March, In: Advanced Organic Chemistry: Reactions, Mechanism, and Structure, 4$^{th}$ Ed., John Wiley & Sons, Inc., New York, 1992, p. 1283). Acrylates 2 and 3, which are particularly suitable for the purposes of this invention, are obtained from heterocyclic methyl ketones 5 by condensation with tert-butoxybis(dimethylamino)methane 6 (Scheme 2).

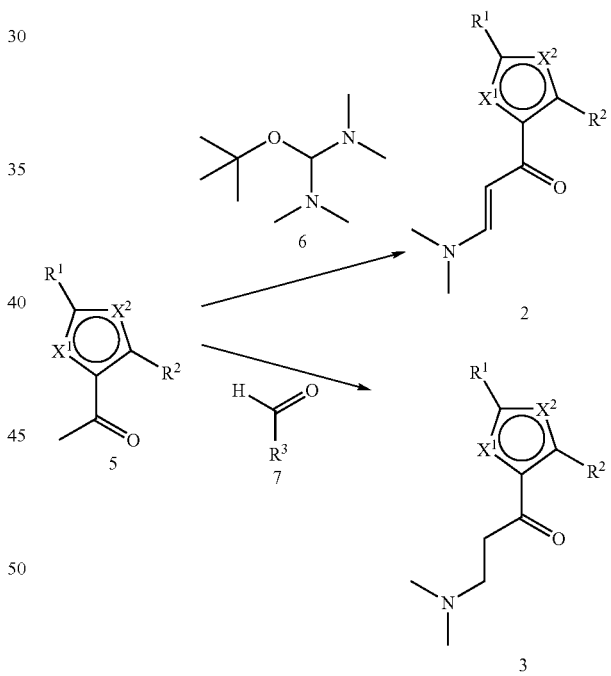

The diamino compounds 4 will be amidines 4a or guanidines 4b, depending on the definition of Z in general structure I. Amidines (HN=CRNH$_2$) can be obtained from readily available amine precursors by condensation with e.g. ketenimines, or by addition of ammonia to suitable nitriles or imidates. Guanidines 4b (Scheme 3) can be elaborated by a number of methods known in the art. For the purposes of this invention, the most useful route is amination of cyanamide 8 with anilines 9.

Scheme 3

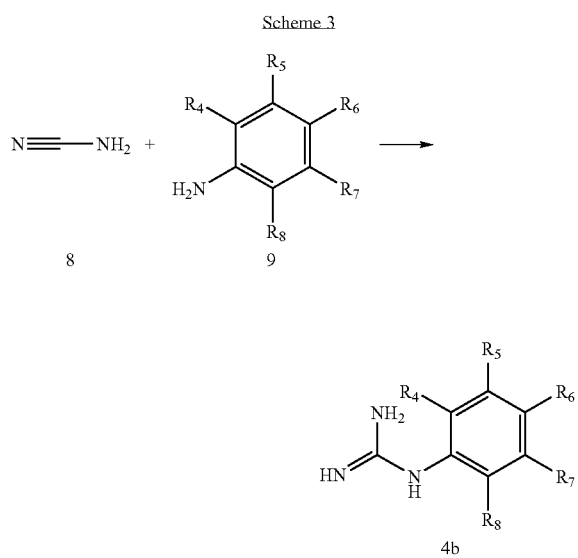

In the case where 5 is a pyrrole, two systems can apply (refer Scheme 4), i.e. the acetyl group which is used to generate the pyrimidine precursors 2 and 3 is either in the pyrrole 3-position (5: $X^1=CR^9$, $X^2=NH$; i.e. structure 5b) or in the pyrrole 2-position ($X^1=NH$, $X^2=CR^9$; i.e. structure 5c).

Scheme 4

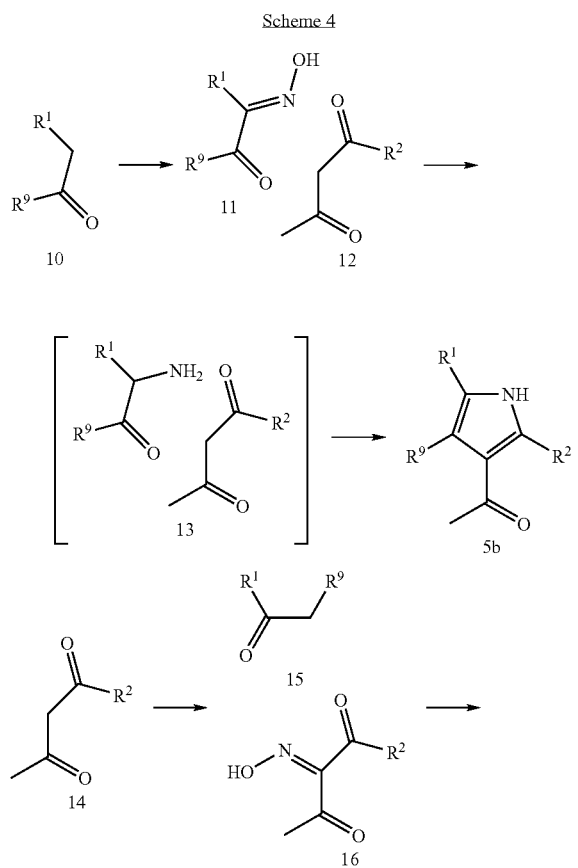

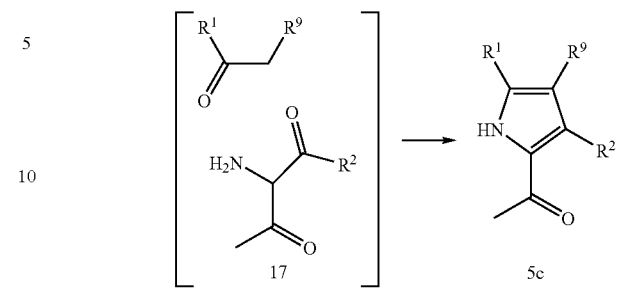

In both cases the pyrrole rings can be assembled using methods known in the art. Particularly relevant is a modification of the Knorr synthesis (refer, e.g J. A. Joule, G. F. Smith, Heterocyclic Chemistry, $2^{nd}$ Ed., Van Nostrand Reinhold (UK) Co. Ltd., 1978, pp.213–215). For the pyrrol-3-yl system, activated (i.e. $R^1$=COOEt, CN, etc.) carbonyl compounds 10 are first nitrosylated. The resulting oximes 11 are condensed with dicarbonyl compounds 12 in the presence of e.g. zinc-acetic acid or aqueous dithionate, with formation of the reactive □-aminocarbonyl intermediate 13. The $R^1$ substituent (e.g. COOEt, CN) in the resulting 3-acetylpyrroles 5b can be further manipulated, either directly, or in the context of intermediates 2 or 3, or in the pyrrolopyrimidine products I. Thus decarboxylation ($R^1$=COOEt) will give products with $R^1$=H, oxidation ($R^1$=CN) will afford products with $R^1$=CONH$_2$, etc. Furthermore, products with $R^1$=H can be transformed into various derivatives, particularly through electrophilic substitution. Thus derivatives where $R^1$ is, for example, a halogen, nitro, amino, alkyl, alkylamino, etc., group can be obtained readily. In the case of the pyrrol-2-yl system an analogous situation arises, here an activating group needs to be present in the carbonyl component 15 (e.g. $R^9$=COOEt, CN, etc.). This is condensed with oximes 16 (derived from dicarbonyl compounds 14), again with formation of the intermediate 17. The $R^9$ substituent in products 5c or derivatives can be manipulated in the same way as the $R^1$ group in the pyrrol-3-yl system discussed above.

Alternatively, compounds of general structure I can be obtained from suitable pyrimidine precursors directly, e.g. from 2,4-disubstituted (halogen, amine, etc.) pyrimidines by successive substitution reactions.

BRIEF DESCRIPTION OF DRAWINGS

The present invention will now be described by way of example and with reference to the following FIGURE.

EXAMPLES

Abbreviations

Figure 1:
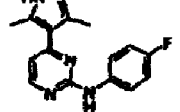
FIG. 1 shows the chemical structure of compounds according to the invention.
Figure 1:
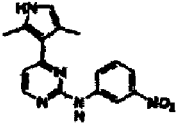
Figure 1:
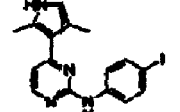
Figure 1:
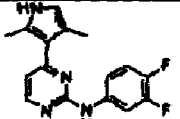
Figure 1:
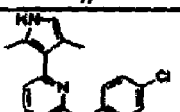
Figure 1:
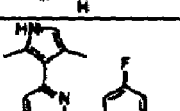
Figure 1:
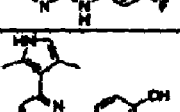
Figure 1:
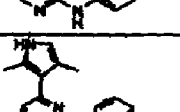
Figure 1:
Figure 1:
Figure 1:
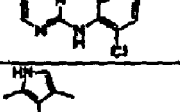
Figure 1:
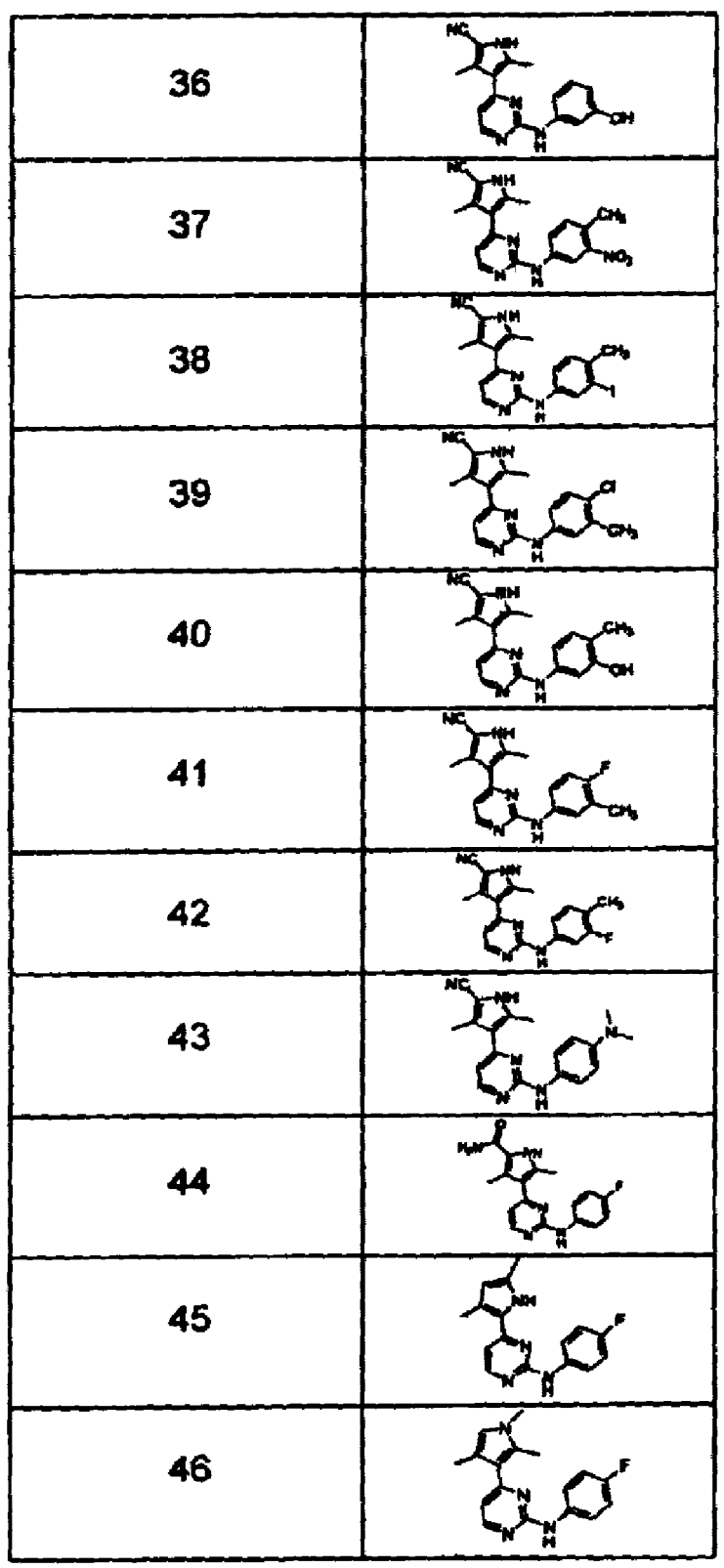
Figure 1:
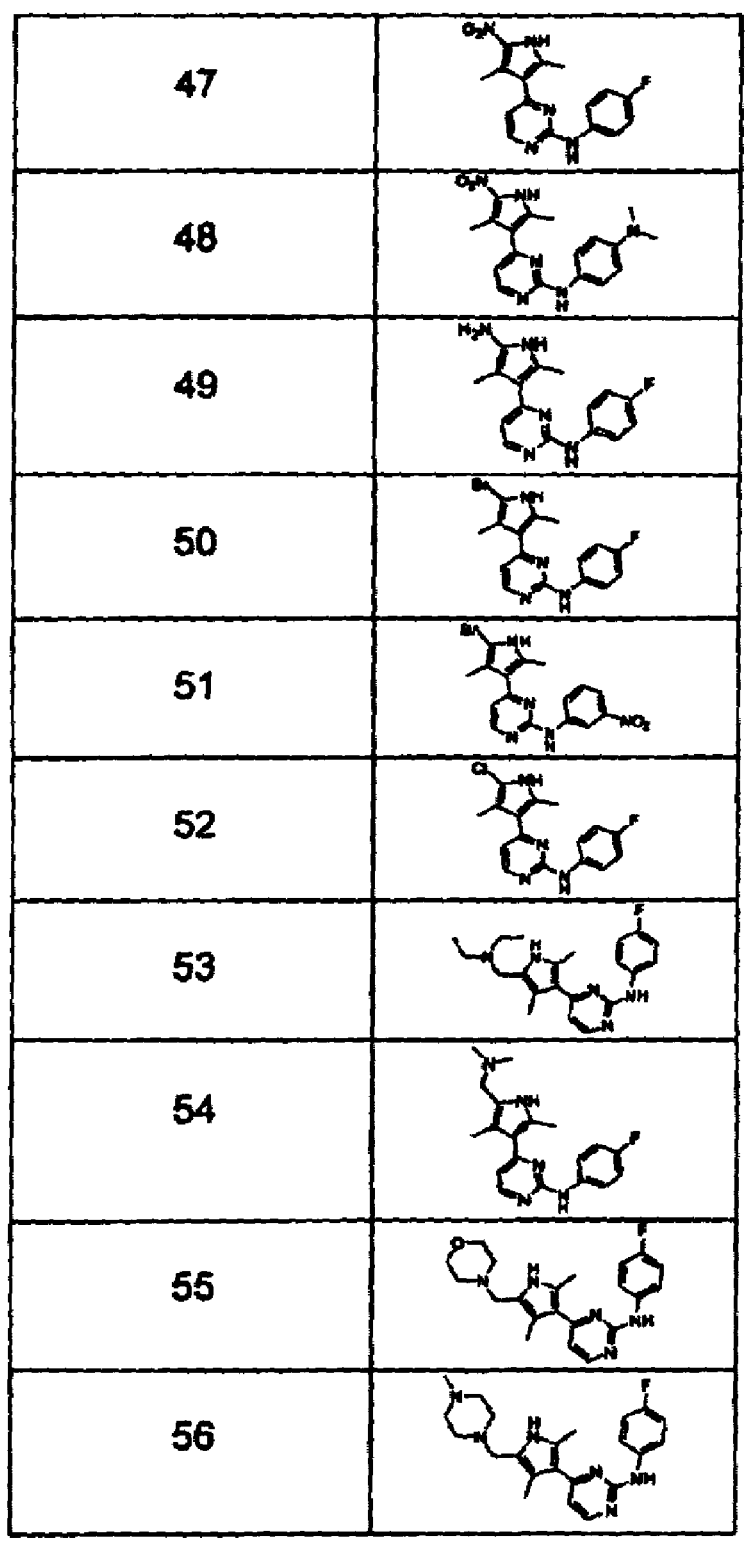

LC-MS, liquid chromatography-mass spectrometry; NMR, nuclear magnetic resonance spectroscopy; r.t. room temperature; PE, petroleum ether (40–60° C. boiling fraction); DMSO, dimethylsulfoxide.

General

NMR spectra were recorded using a Bruker DPX-300 instrument. Chemical shifts are reported in ppm (δ) from tetramethylsilane. EM Kieselgel 60 (0.040–0.063 mm) was used for flash column chromatography. Melting points were determined with a LEICA testo-720 electrothermometer and are uncorrected. Compound numbers are shown in brackets, where appropriate.

Example 1

3-Dimethylamino-1-(2,4-dimethyl-1H-pyrrol-3-yl)-propenone

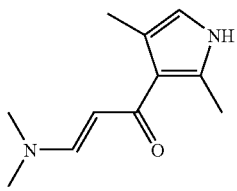

A mixture of 1-(2,4-dimethyl-1H-pyrrol-3-yl)-ethanone (2 g, 15 mmol) in 5 mL of 1,1-bis-dimethylamino-3,3-dimethyl-butan-2-one was heated at 100° C. for 22 h. The precipitates of the reaction mixture were slurried in EtOAc/PE with chilling. The crude product was filtered, washed with EtOAc/PE, and dried in vacuo to afford the title compound as a purple solid (2.6 g). $^1$H-NMR (CDCl$_3$) δ: 2.25 (s, 6H, CH$_3$), 2.45 (s, 6H, CH$_3$), 5.46 (d, 1H, J=12.6 Hz, CH), 6.35 (s, 1H, pyrrolyl-H), 7.63 (d, 1H, J=12.6 Hz, CH).

Example 2

[4-(2,4-Dimethyl-1H-pyrrol-3-yl)-pyrimidin-2-yl]-(4-fluoro-phenyl)-amine [1]

To a mixture of 3-dimethylamino-1-(2,4-dimethyl-1H-pyrrol-3-yl)-propenone (1 mmol, 0.19 g) and 4-fluorophenyl guanidine nitrate (2 mmol, 0.44 g) in 2-methoxyethanol (5 mL) was added NaOH (40 mg). The reaction mixture was heated at 100–120° C. under N$_2$ for 6 h. The solvent was evaporated to dryness and the residue was purified by flash chromatography (1:2 EtOAc/PE). Recrystallisation from EtOAc/PE afforded the title compound (174 mg, 62%) as brown crystals. $^1$H-NMR (CDCl$_3$) δ: 2.21 (s, 3H, CH$_3$), 2.43 (s, 3H, CH$_3$), 6.33 (s, 1H, pyrrolyl-H), 6.73 (d, 1H, J=5.3 Hz, pyrimidinyl-H), 7.00 (m, 2H, Ph-H), 7.79 (m, 2H, Ph-H), 8.28 (d, 1H, J=5.3 Hz, pyrimidinyl-H), 9.16 (s, 1H, NH), 10.59 (s, 1H, NH).

The following compounds were prepared in a manner analogous to that described above:

[4-(2,4-Dimethyl-1H-pyrrol-3-yl)-pyrimidin-2-yl-(3-nitro-phenyl)-amine [2]

Yellow-orange solid. M.p. 197–199° C. LC-MS: m/z=310 (M+1). C$_{16}$H$_{15}$N$_5$O$_2$ requires C, 62.12; H, 4.89; N, 22.64; found C, 62.61; H, 4.99; N, 22.20. $^1$H-NMR (CDCl$_3$) δ: 2.71 (d, 6H, CH$_3$), 7.05 (d, 1H, J=5.3 Hz, pyrimidinyl-H), 7.47 (m, 2H, Ph-H), 7.78 (m, 1H, Ph-H), 7.81 (s, 1H, Ar—H), 8.07 (m, 1H, Ph-H), 8.51 (d, 1H, J=5.3 Hz, pyrimidinyl-H), 8.99 (br. s, 1H, NH), 9.91 (br. s, 1H, NH).

[4-(2,4-Dimethyl-1H-pyrrol-3-yl)-pyrimidin-2-yl]-(4-iodo-phenyl)-amine [3]

$^1$H-NMR (CDCl$_3$) δ: 2.26 (s, 3H, CH$_3$), 2.48 (s, 3H, CH$_3$), 6.80 (d, 1H, J=5.3 Hz, pyrimidinyl-H), 7.47 (m, 2H, Ph-H), 7.57 (m, 2H, Ph-H), 7.23 (s, 1H, pyrrolyl-H), 8.32 (d, 1H, J=5.3 Hz, pyrimidinyl-H).

(3,4-Difluoro-phenyl)-[4-(2,4-dimethyl-1H-pyrrol-3-yl)-pyrimidin-2-yl]-amine [4]

$^1$H-NMR (CDCl$_3$) δ: 2.23 (s, 3H, CH$_3$), 2.46 (s, 3H, CH$_3$), 6.42 (m, 1H, pyrrolyl-H), 6.77 (d, 1H, J=5.3 Hz, pyrimidinyl-H), 7.11 (m, 1H, Ph-H), 7.41 (m, 1H, Ph-H), 8.05 (m, 1H, Ph-H), 8.29 (d, 1H, J=5.3 Hz, pyrimidinyl-H), 9.21 (s, 1H, Ph-H), 10.46 (br. s, 1H, NH).

(4-Chloro-phenyl)-[4-(2,4-dimethyl-1H-pyrrol-3-yl)-pyrimidin-2-yl]-amine [5]

M.p. 219–223° C. MS: [M+H]$^+$=299.4 (C$_{16}$H$_{15}$ClN$_4$ requires 298.8). $^1$H-NMR (DMSO-d$_6$) δ: 2.19 (s, 3H, CH$_3$), 2.42 (s, 3H, CH$_3$), 6.48 (s, 1H, pyrrolyl-H), 6.82 (d, 1H, J=5.3 Hz, pyrimidinyl-H), 7.31 (d, 2H, J=8.7 Hz, Ph-H), 7.84 (d, 2H, J=8.7 Hz, Ph-H), 8.34 (d, 1H, J=5.3 Hz, pyrimidinyl-H), 9.45 (s, 1H, NH), 10.72 (br. s, 1H, NH).

(3,5-Difluoro-phenyl)-[4-(2,4-dimethyl-1H-pyrrol-3-yl)-pyrimidin-2-yl]-amine [6]

M.p. 153.3–156.8° C. MS: [M+H]$^+$=303.6 (C$_{16}$H$_{14}$F$_2$N$_4$ requires 300.3). $^1$H-NMR (CD$_3$OD) δ: 2.25 (s, 3H, CH$_3$), 2.47 (s, 3H, CH$_3$), 6.42–6.48 (m, 2H, pyrrolyl-H and Ph-H), 6.80 (d, 1H, J=5.5 Hz, pyrimidinyl-H), 7.44–7.48 (m, 2H, Ph-H), 8.31 (d, 1H, J=5.5 Hz, pyrimidinyl-H).

4-[4-(2,4-Dimethyl-1H-pyrrol-3-yl)-pyrimidin-2-ylamino]-phenol [7]

M.p. 189.5–193.4° C. MS: [M+H]$^+$=281.9 (C$_{16}$H$_{16}$N$_4$O requires 280.3). $^1$H-NMR (CD$_3$OD) δ: 2.23 (s, 3H, CH$_3$), 2.43 (s, 3H, CH$_3$), 6.44 (s, 1H, pyrrolyl-H), 6.75–6.78 (m, 3H, pyrimidinyl-H and Ph-H), 7.39 (d, 2H, J=8.8 Hz, Ph-H), 8.17 (d, 1H, J=5.3 Hz, pyrimidinyl-H).

3-[4-(2,4-Dimethyl-1H-pyrrol-3-yl)-pyrimidin-2-ylamino]-phenol [8]

M.p. 169.0–174.6° C. MS: [M+H]$^+$=281.3 (C$_{16}$H$_{16}$N$_4$O requires 280.3). $^1$H-NMR (CD$_3$OD) δ: 2.26 (s, 3H, CH$_3$), 2.47 (s, 3H, CH$_3$), 6.44–6.48 (m, 2H, pyrrolyl-H, Ph-H 6.84 (d, 1H, J=5.4 Hz, pyrimidinyl-H), 7.05–7.10 (m, 2H, Ph-H), 7.32 (m, 1H, Ph-H), 8.25 (d, 1H, J=5.3 Hz, pyrimidinyl-H).

(2,4-Difluoro-phenyl)-[4-(2,4-dimethyl-1H-pyrrol-3-yl)-pyrimidin-2-yl]-amine [9]

M.p. 219–220° C. MS: [M+H]$^+$=302.6 (C$_{16}$H$_{14}$F$_2$N$_2$ requires 300.3). $^1$H-NMR (DMSO-d$_6$) δ: 2.10 (s, 3H, CH$_3$), 2.36 (s, 3H, CH$_3$), 6.43 (s, 1H, pyrrolyl-H), 6.77 (d, 1H, J=5.3 Hz, pyrimidinyl-H), 7.06 (m, 1H, Ph-H), 7.27 (m, 1H, Ph-H), 7.66 (m, 1H, Ph-H), 8.25 (d, 1H, J=5.3 Hz, pyrimidinyl-H), 8.71 (s, 1H, Ph-H), 10.70 (br. s, 1H, NH).

(2,4-Dichloro-phenyl)-[4-(2,4-dimethyl-1H-pyrrol-3-yl)-pyrimidin-2-yl]-amine [10]

M.p. 158.5–159.7° C. MS: [M+H]⁺=335.4 (C₁₆H₁₄Cl₂N₄ requires 333.2). ¹H-NMR (DMSO-d₆) δ: 2.18 (s, 3H, CH₃), 2.38 (s, 3H, CH₃), 6.51 (s, 1H, pyrrolyl-H), 6.90 (d, 1H, J=5.5 Hz, pyrimidinyl-H), 7.46 (m, 1H, Ph-H), 7.71 (m, 1H, Ph-H), 8.05 (m, 1H, Ph-H), 8.36 (d, 1H, J=5.3 Hz, pyrimidinyl-H), 8.49 (s, 1H, Ph-H), 10.80 (br. s, 1H, NH).

(4-Chloro-3-trifluoromethyl-phenyl)-[4-(2,4-dimethyl-1H-pyrrol-3-yl)-pyrimidin-2-yl]-amine [11]

M.p. 187.7–190.7° C. MS: [M+H]⁺=368.6 (C₁₇H₁₄ClF₃N₄ requires 366.8). ¹H-NMR (DMSO-d₆) δ: 2.19 (s, 3H, CH₃), 2.42 (s, 3H, CH₃), 6.50 (s, 1H, pyrrolyl-H), 6.89 (d, 1H, J=5.3 Hz, pyrimidinyl-H), 7.61 (m, 1H, Ph-H), 8.08 (m, 1H, Ph-H), 8.39–8.42 (m, 2H, Ph-H and pyrimidinyl-H), 9.79 (s, 1H), 10.80 (br. s, 1H, NH).

[4-(2,4-Dimethyl-1H-pyrrol-3-yl)-pyrimidin-2-yl]-(4-trifluoromethyl-phenyl)-amine [12]

M.p. 165.6–167.9° C. MS: [M+H]⁺=332.9 (C₁₇H₁₅F₃N₄ requires 332.3). ¹H-NMR (DMSO-d₆) δ: 2.26 (s, 3H, CH₃), 2.49 (s, 3H, CH₃), 6.56 (s, 1H, pyrrolyl-H), 6.94 (d, 1H, J=5.3 Hz, pyrimidinyl-H), 7.67 (d, 2H, J=8.5 Hz, Ph-H), 8.09 (d, 2H, J=8.5 Hz, Ph-H), 8.45 (d, 1H, J=5.3 Hz, pyrimidinyl-H), 9.82 (s, 1H, NH).

[4-(2,4-Dimethyl-1H-pyrrol-3-yl)-pyrimidin-2-yl]-(3-trifluoromethyl-phenyl)-amine [13]

M.p. 152.7–154.3° C. MS: [M+H]⁺=332.6 (C₁₇H₁₅F₃N₄ requires 332.3). ¹H-NMR (DMSO-d₆) δ: 2.26 (s, 3H, CH₃), 2.48 (s, 3H, CH₃), 6.56 (s, 1H, pyrrolyl-H), 6.92 (d, 1H, J=5.3 Hz, pyrimidinyl-H), 7.29 (m, 1H, Ph-H), 7.55 (m, 1H, Ph-H), 8.03 (m, 1H, Ph-H), 8.42–7.45 (m, 2H, pyrimidinyl-H and Ph-H), 9.73 (s, 1H, NH), 10.83 (br. s, 1H, NH).

(3-Chloro-phenyl)-[4-(2,4-dimethyl-1H-pyrrol-3-yl)-pyrimidin-2-yl]-amine [14]

M.p. 140.4–144.2° C. MS: [M+H]⁺=299.5 (C₁₆H₁₅ClN₄ requires 298.8). ¹H-NMR (DMSO-d₆) δ: 2.21 (s, 3H, CH₃), 2.44 (s, 3H, CH₃), 6.51 (s, 1H, pyrrolyl-H), 6.85 (d, 1H, J=5.3 Hz, pyrimidinyl-H), 6.94 (d, 1H, J=7.6 Hz, Ph-H), 7.28 (t, 1H, J=8.1 Hz, Ph-H), 7.61 (d, 1H, J=8.2 Hz, Ph-H), 8.19 (s, 1H, Ph-H), 8.37 (d, 1H, J=5.3 Hz, pyrimidinyl-H), 9.55 (s, 1H, NH), 10.78 (br. s, 1H, NH).

N-[4-(2,4-Dimethyl-H-pyrrol-3-yl)-pyrimidin-2-yl]-N',N'-dimethyl-benzene-1,4-diamine [15]

M.p. 179.9–182.1° C. MS: [M+H]⁺=307.3 (C₁₈H₂₁N₅ requires 307.4). ¹H-NMR (CDCl₃) δ: 2.25 (s, 3H, CH₃), 2.46 (s, 3H, CH₃), 2.91 (s, 6H, CH₃), 6.46 (s, 1H, pyrrolyl-H), 6.70 (d, 1H, J=5.1 Hz, pyrimidinyl-H), 6.78 (dd, 2H, J=6.8, 2.2 Hz, Ph-H), 6.79 (br. s, 1H, NH), 7.45 (dd, 2H, J=6.8, 2.2 Hz, Ph-H), 7.80 (br. s, 1H, NH), 8.28 (d, 1H, J=5.1 Hz, pyrimidinyl-H).

(3-Chloro-4-iodo-phenyl)-[4-(2,4-dimethyl-1H-pyrrol-3-yl)-pyrimidin-2-yl]-amine [16]

M.p. 185.0–187.4° C. MS: [M+H]⁺=423.9 (C₁₆H₁₄ClIN₄ requires 424.7). ¹H-NMR (DMSO-d₆) δ: 2.18 (s, 3H, CH₃), 2.41 (s, 3H, CH₃), 6.48 (s, 1H, pyrrolyl-H), 6.84 (d, 1H, J=5.4 Hz, pyrimidinyl-H), 7.40 (dd, 1H, J=8.8, 2.4 Hz, Ph-H), 7.75 (d, 1H, J=8.8 Hz, Ph-H), 8.34 (m, 1H, Ph-H), 8.36 (d, 1H, J=5.4 Hz, pyrimidinyl-H), 9.61 (s, 1H, NH), 10.75 (s, 1H, NH).

[4-(2,4-Dimethyl-1H-pyrrol-3-yl)-pyrimidin-2-yl]-(3-fluoro-4-iodo-phenyl)-amine [17]

M.p. 200–202° C. MS: [M+H]⁺=407.4 (C₁₆H₁₄FIN₄ requires 408.2). ¹H-NMR (DMSO-d₆) δ: 2.18 (s, 3H, CH₃), 2.40 (s, 3H, CH₃), 6.48 (s, 1H, pyrrolyl-H), 6.84 (d, 1H, J=5.4 Hz, pyrimidinyl-H), 7.35 (m, 1H, Ph-H), 7.64, (t, 1H, J=8.0 Hz, Ph-H), 8.02 (dd, 1H, J=12.0, 2.2 Hz, Ph-H), 8.36 (d, 1H, J=5.4 Hz, pyrimidinyl-H), 9.65 (s, 1H, NH), 10.75 (s, 1H, NH).

Example 3

4-(3-Dimethylamino-acryloyl)-3,5-dimethyl-1H-pyrrole-2-carbonitrile

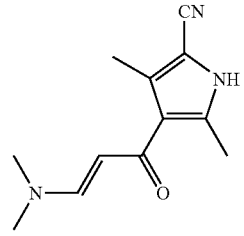

Ethyl cyanoacetate (10 mL, 94 mmol) was diluted with AcOH (20 mL) and the solution was cooled to −10° C. (ice-MeOH bath). NaNO₂ (6.5 g, 94 mmol) was dissolved in H₂O (10 mL) and the solution was added dropwise over a period of 40 min, keeping the internal temperature <0° C. After completion of the addition, the reaction mixture was stirred for 1 h with cooling. It was then warmed to room temperature and stirred for a further 3 h. The mixture was diluted with acetic acid (50 mL) and H₂O (50 mL). Pentane-2,4-dione (10.6 mL, 103 mmol) was added and the mixture heated to ~75° C. To this reaction mixture Zn powder (6.9 g, 105 mmol) was added in portions over a period of 30 min at such a rate as to maintain the internal temperature <90° C. The reaction mixture was then heated for a further 30 min before pouring into H₂O (1 mL). From the reaction mixture 3,5-dimethyl-1H-pyrrole-2-carbonitrile (3.67 g) was filtered as an off-white solid. The filtrate was extracted with EtOAc (3×500 mL). The combined organic extracts were washed (brine) and dried (MgSO₄). The solvent was evaporated to a brown oil, which was purified by chromatography (100 g SiO₂, eluted with 4:1 heptane/EtOAc) to afford a further crop (4.41 g) of this product as a pale yellow solid (total yield 72%).

3,5-Dimethyl-1H-pyrrole-2-carbonitrile (1.2 g, 10 mmol) was dissolved in anhydrous 1,2-dichloroethane (15 mL) and AlCl₃ (2.93 g, 22 mmol) was added proportion-wise. The reaction vessel was purged with N₂ and was cooled in an ice-water bath. AcCl (0.71 mL, 10 mmol) was added dropwise and the mixture was stirred for 1 h with cooling and for a further 3 h at room temperature. The reaction mixture was quenched by careful addition of 2 M aq HCl. The acidity of the mixture was adjusted to approximately pH 6 by addition of NaHCO$_3$. After separation of the organic phase, the aqueous phase was extracted with EtOAc (3×100 mL). The combined organic phases were washed (H$_2$O, then brine), dried (MgSO$_4$), and filtered. The solvent was evaporated to afford of 4-acetyl-3,5-dimethyl-1H-pyrrole-2-carbonitrile (1.42 g, 88%) as a pale tan solid. $^1$H-NMR (CDCl$_3$) δ: 2.44 (s, 3H, CH$_3$), 2.45 (s, 3H, CH$_3$), 2.54 (s, 3H, CH$_3$), 8.75 (br. s, 1H, NH).

4-Acetyl-3,5-dimethyl-1H-pyrrole-2-carbonitrile (1.38 g, 8.51 mmol) was suspended in 1,1-bis-dimethylamino-3,3-dimethyl-butan-2-one (1.3 mL) and heated at 75° C. for 42 h. The reaction mixture was evaporated to dryness and the residue was purified by SiO$_2$ chromatography (heptane/EtOAc) to afford the title compound (1.2 g, 65%) as a pale tan solid. $^1$H-NMR (DMSO-d$_6$) δ: 2.21 (s, 3H, CH$_3$), 2.31 (s, 3H, CH$_3$), 3.32 (s, 6H, CH$_3$), 5.22 (d, 1H, J=12.4 Hz, CH), 7.47 (d 1H, J=12.4 Hz, CH), 11.96 (br. s, 1H, NH).

Example 4

3,5-Dimethyl-4-[2-(3-nitro-phenylamino)-pyrimidin-4-yl]-1H-pyrrole-2-carbonitrile [31]

To a mixture of 4-(3-dimethylamino-acryloyl)-3,5-dimethyl-1H-pyrrole-2-carbonitrile (1.0 mmol, 0.22 g) and 3-nitrophenyl guanidine nitrate (1.5 mmol, 0.36 g) in 2-methoxyethanol (5 mL) was added K$_2$CO$_3$ (138 mg, 1.0 mmol). The reaction mixture was heated at 120° C. under N$_2$ for 18 h. The solvent was evaporated to dryness and the residue was purified by flash chromatography (1:2 EtOAc/heptane) to afford the title compound as a light-yellow solid. M.p. 258–259° C. MS: [M+H]$^+$=336.1 (C$_{17}$H$_{14}$N$_6$O$_2$ requires 334.3). $^1$H-NMR (CD$_3$OD) δ: 2.39 (s, 3H, CH$_3$), 2.49 (s, 3H, CH$_3$), 6.94 (d, 1H, J=5.1 Hz, pyrimidinyl-H), 7.50 (t, 1H, J=8.3 Hz, Ph-H), 7.81 (m, 1H, Ph-H), 7.94 (m, 1H, Ph-H), 8.45 (d, 1H, J=5.1 Hz, pyrimidinyl-H), 8.94 (t, 1H, J=2.2 Hz, Ph-H).

The following compounds were prepared in a manner analogous to that described above:

4-[2-(4-Fluoro-phenylamino)-pyrimidin-4-yl]-3,5-dimethyl-1H-pyrrole-2-carbonitrile [32]

MS: [M+H]$^+$=307.7 (C$_{17}$H$_{14}$FN$_5$ requires 307.3). $^1$H-NMR (DMSO-d$_6$) δ: 2.30 (s, 3H, CH$_3$), 2.40 (s, 3H, CH$_3$), 6.84 (d, 1H, J=5.0 Hz, pyrimidinyl —H), 7.00 (m, 2H, Ph-H), 7.73 (m, 2H, Ph-H), 8.40 (d, 1H, J=5.5 Hz, pyrimidinyl —H), 9.46 (s, 1H, NH), 12.19 (br. s, 1H, NH).

4-[2-(4-Hydroxy-phenylamino)-pyrimidin-4-yl]-3,5-dimethyl-1H-pyrrole-2-carbonitrile [33]

M.p. 272–276° C. MS: [M+H]$^+$=305.8 (C$_{17}$H$_{15}$N$_5$O requires 305.3). $^1$H-NMR (CD$_3$OD) δ: 2.33 (s, 3H, CH$_3$), 2.41 (s, 3H, CH$_3$), 6.74–6.56 (m, 3H, pyrimidinyl-H/Ph-H), 7.36 (d, 2H, J=8.5 Hz, Ph-H), 8.25 (d, 1H, J=5.4 Hz, pyrimidinyl-H).

3,5-Dimethyl-4-[2-(4-trifluoromethyl-phenylamino)-pyrimidin-4-yl]-H-pyrrole-2-carbonitrile [34]

M.p. 195.6–198.9° C. MS: [M+H]$^+$=357.7 (C$_{18}$H$_{14}$F$_3$N$_5$ requires 357.3). $^1$H-NMR (CDCl$_3$) δ: 2.33 (s, 3H, CH$_3$), 2.44 (s, 3H, CH$_3$), 6.75 (d, 1H, J=5.1 Hz, pyrimidinyl-H), 7.20 (br. s, 1H, NH), 7.50 (d, 2H, J=8.8 Hz, Ph-H), 7.71 (d, 2H, J=8.8 Hz, Ph-H), 8.39 (d, 1H, J=5.1 Hz, pyrimidinyl), 8.40 (br. s, 1H, NH).

4-[2-(4-Iodo-phenylamino)-pyrimidin-4-yl]-3,5-dimethyl-1H-pyrrole-2-carbonitrile [35]

M.p. 178.3–181.2° C. MS: [M+H]$^+$=416.6 (C$_{18}$H$_{141}$N$_5$ requires 415.2). $^1$H-NMR (CDCl$_3$) δ: 2.39 (s, 3H, CH$_3$), 2.49 (s, 3H, CH$_3$), 6.76 (d, 1H, J=5.1 Hz, pyrimidinyl-H), 7.10 (br. s, 1H, NH), 7.44 (d, 2H, J=8.8 Hz, Ph-H), 7.61 (d, 2H, J=8.8 Hz, Ph-H), 8.42 (d, 1H, J=5.1 Hz, pyrimidinyl-H), 8.45 (br. s, 1H, NH).

4-[2-(3-Hydroxy-phenylamino)-pyrimidin-4-yl]-3,5-dimethyl-1H-pyrrole-2-carbonitrile [36]

M.p. 247–250° C. MS: [M+H]$^+$=305.8 (C$_{17}$H$_{15}$N$_5$O requires 305.3). $^1$H-NMR (DMSO-d$_6$) δ: 2.31 (s, 3H, CH$_3$), 2.41 (s, 3H, CH$_3$), 6.33 (m, 1H, Ph-H), 6.82 (d, 1H, J=5.1 Hz, pyrimidinyl-H), 7.01 (t, 1H, J=8.1 Hz, Ph-H), 7.11 (m, 1H, Ph-H), 7.33 (t, 1H, J=2.1 Hz, Ph-H), 8.40 (d, 1H, J=5.4 Hz, pyrimidinyl-H), 9.18 (s, 1H), 9.30 (s, 1H), 12.20 (br. s, 1H, NH).

3,5-Dimethyl-4-[2-(4-methyl-3-nitro-phenylamino)-pyrimidin-4-yl]-1H-pyrrole-2-carbonitrile [37]

M.p. 233–237° C. MS: [M+H]$^+$=350.0 (C$_{18}$H$_{16}$N$_6$O$_2$ requires 348.6). $^1$H-NMR (DMSO-d$_6$) δ: 2.31 (s, 3H, CH$_3$), 2.42 (s, 3H, CH$_3$), 2.44 (s, 3H, CH$_3$), 6.92 (d, 1H, J=5.4 Hz, pyrimidinyl-H), 7.39 (d, 1H, J=8.5 Hz, Ph-H), 7.87 (dd, 1H, J=8.1, 1.7 Hz, Ph-H), 8.48 (d, 1H, J=5.1 Hz, pyrimidinyl-H), 8.63 (d, 1H, J=1.7 Hz, Ph-H), 9.87 (s, 1H, NH), 12.21 (br. s, 1H, NH).

4-[2-(3-Iodo-4-methyl-phenylamino)-pyrimidin-4-yl]-3,5-dimethyl-1H-pyrrole-2-carbonitrile [38]

M.p. 189.5–191.7° C. MS: [M+H]$^+$=431.5 (C$_{18}$H$_{161}$N$_5$ requires 429.6). $^1$H-NMR (DMSO-d$_6$) δ: 2.29 (s, 3H, CH$_3$), 2.32 (s, 3H, CH$_3$), 2.43 (s, 3H, CH$_3$), 6.85 (d, 1H, J=5.1 Hz, pyrimidinyl-H), 7.20 (d, 1H, J=8.1 Hz, Ph-H), 7.57 (m, 1H, Ph-H), 8.41–8.43 (m, 2H, Ph-H, pyrimidinyl-H), 9.48 (s, 1H, NH), 12.20 (br. s, 1H, NH).

4-[2-(4-Chloro-3-methyl-phenylamino)-pyrimidin-4-yl]-3,5-dimethyl-1H-pyrrole-2-carbonitrile [39]

M.p. 194.2–197.9° C. MS: [M+H]$^+$=338.0 (C$_{18}$H$_{16}$ClN$_5$ requires 337.8). $^1$H-NMR (DMSO-d$_6$) δ: 2.27 (s, 3H, CH$_3$), 2.31 (s, 3H, CH$_3$), 2.41 (s, 3H, CH$_3$), 6.86 (d, 1H, J=5.4 Hz, pyrimidinyl-H), 7.28 (d, 1H, J=8.5 Hz, Ph-H), 7.61 (dd, 1H, J=8.8, 2.4 Hz, Ph-H), 7.73 (d, 1H, J=2.7 Hz, Ph-H), 8.43 (d, 1H, J=5.1 Hz, pyrimidinyl-H), 9.51 (s, 1H, NH), 12.21 (br. s, 1H, NH).

4-[2-(3-Hydroxy-4-methyl-phenylamino)-pyrimidin-4-yl]-3,5-dimethyl-1H-pyrrole-2-carbonitrile [40]

M.p. 221–225° C. MS: [M+H]$^+$=320.9 (C$_{18}$H$_{17}$N$_5$O requires 319.4). $^1$H-NMR (DMSO-d$_6$) δ: 2.03 (s, 3H, CH$_3$), 2.29 (s, 3H, CH$_3$), 2.40 (s, 3H, CH$_3$), 6.78 (d, 1H, J=5.1 Hz, pyrimidinyl-H), 6.89 (d, 1H, J=8.1 Hz, Ph-H), 7.02 (dd, 1H, J=8.3, 1.7 Hz, Ph-H), 7.29 (d, 1H, J=0.7 Hz, Ph-H), 8.37 (d, 1H, J=4.9 Hz, pyrimidinyl-H), 9.08 (s, 1H), 9.20 (s, 1H), 12.17 (br. s, 1H, NH).

4-[2-(4-Fluoro-3-methyl-phenylamino)-pyrimidin-4-yl]-3,5-dimethyl-1H-pyrrole-2-carbonitrile [41]

M.p. 161.3–164.1° C. MS: [M+H]$^+$=321.6 (C$_{18}$H$_{16}$FN$_5$ requires 321.4). $^1$H-NMR (DMSO-d$_6$) δ: 2.19 (s, 3H, CH$_3$), 2.30 (s, 3H, CH$_3$), 2.42 (s, 3H, CH$_3$), 6.82 (d, 1H, J=5.1 Hz, pyrimidinyl-H), 7.03 (t, 1H, J=9.3 Hz, Ph-H), 7.53 (m, 1H, Ph-H), 7.61 (dd, 1H, J=7.1, 2.4 Hz, Ph-H), 8.39 (d, 1H, J=5.1 Hz, pyrimidinyl-H), 9.36 (s, 1H, NH), 12.20 (br. s, 1H, NH).

4-[2-(3-Fluoro-4-methyl-phenylamino)-pyrimidin-4-yl]-3,5-dimethyl-1H-pyrrole-2-carbonitrile [42]

M.p. 177.7–179.9° C. MS: [M+H]$^+$=322.5 (C$_{18}$H$_{16}$FN$_5$ requires 321.3). $^1$H-NMR (DMSO-d$_6$) δ: 2.15 (s, 3H, CH$_3$), 2.30 (s, 3H, CH$_3$), 2.43 (s, 3H, CH$_3$), 6.86 (d, 1H, J=5.1 Hz, pyrimidinyl-H), 7.13 (t, 1H, J=9.0 Hz, Ph-H), 7.36 (dd, 1H, J=8.1, 1.7 Hz, Ph-H), 7.75 (dd, 1H, J=12.9, 1.5 Hz, Ph-H), 8.43 (d, 1H, J=5.4 Hz, pyrimidinyl-H), 9.56 (s, 1H, NH), 12.21 (br. s, 1H, NH).

4-[2-(4-Dimethylamino-phenylamino)-pyrimidin-4-yl]-3,5-dimethyl-1H-pyrrole-2-carbonitrile [43]

M.p. 190.6–193.7° C. MS: [M+H]$^+$=334.7 (C$_{19}$H$_{20}$N$_6$ requires 332.4). $^1$H-NMR (CDCl$_3$) δ: 2.36 (s, 3H, CH$_3$), 2.46 (s, 3H, CH$_3$), 2.94 (br. s, 6H, CH$_3$), 6.66 (d, 1H, J=5.6 Hz, pyrimidinyl-H), 6.79–6.80 (m, 2H, Ph-H), 7.05 (br. s, 1H, NH), 7.40–7.43 (m, 2H, Ph-H), 8.34 (d, 1H, J=5.1 Hz, pyrimidinyl-H), 8.52 (br. s, 1H, NH).

Example 5

4-(3-Dimethylamino-acryloyl)-3,5-dimethyl-1H-pyrrole-2-carboxylic acid amide

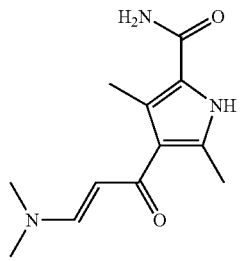

1-(2,4-Dimethyl-1H-pyrrol-3-yl)-ethanone (1.1 g, 10 mmol) was partially dissolved in 2 M solution of ammonia in MeOH and H$_2$O$_2$ (10 mL of a 27% w/w solution in H$_2$O) was added dropwise over a period of 40 min at such a rate as to maintain the internal temperature ≦30° C. The mixture was stirred for 18 h at room temperature. The resulting suspended white solid was filtered and recrystallised from EtOAc to afford 4-acetyl-3,5-dimethyl-1H-pyrrole-2-carboxylic acid amide (1.06 g). An aliquot (720 mg, 4 mmol) was suspended in 1,1-bis-dimethylamino-3,3-dimethyl-butan-2-one (2 mL, 9.6 mmol) in a N$_2$-flushed flask and heated at 75° C. for 48 h. The crude mixture was cooled and purified by SiO$_2$ chromatography (EtOAc/MeOH gradient elution). The title compound (449 mg) was obtained as a buff solid. $^1$H-NMR (DMSO-d$_6$) δ: 2.30 (s, 3H, CH$_3$), 2.46 (s, 3H, CH$_3$), 2.90 (br. s, 2H, NH), 3.09 (s, 3H, CH$_3$), 3.13 (s, 3H, CH$_3$), 5.23 (d, 1H, J=12.4 Hz, CH), 7.38 (d, 1H, J=12.7 Hz, CH), 10.97 (br. s, 1H, NH).

Example 6

4-[2-(4-Fluoro-phenylamino)-pyrimidin-4-yl]-3,5-dimethyl-1H-pyrrole-2-carboxylic acid amide [44]

4-(3-Dimethylamino-acryloyl)-3,5-dimethyl-1H-pyrrole-2-carboxylic acid amide (100 mg, 0.43 mmol), 4-fluorophenylguanidine nitrate (139 mg, 0.65 mmol) and K$_2$CO$_3$ (94 mg, 0.68 mmol) were partially dissolved in 2-methoxyethanol (5 mL) and heated at 120° C. for 18 h. The mixture was concentrated in vacuo and purified by SiO$_2$ chromatography (EtOAc/MeOH gradient elution). The crude product was triturated in iPr$_2$O to afford the title compound (31 mg) as a buff solid. M.p. 93.5–96.8° C. MS: [M+H$^+$]=326.9 (C$_{17}$H$_{16}$FN$_5$O requires 325.3). $^1$H-NMR (DMSO-d$_6$) δ: 2.36 (s, 3H, CH$_3$), 2.39 (s, 3H, CH$_3$), 6.79 (d, 1H, J=5.4 Hz, pyrimidinyl-H), 6.92 (br. s, 2H, NH), 7.07 (t, 2H, J=8.5 Hz, Ph-H), 7.76–7.78 (m, 2H, Ph-H), 8.36 (d, 1H, J=5.4 Hz, pyrimidinyl-H), 9.41 (s, 1H, NH), 11.24 (br. s, 1H, NH).

Example 7

3-Dimethylamino-1-(3,5-dimethyl-1H-pyrrol-2-yl)-propenone

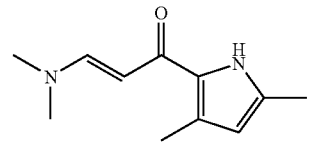

Pentane-2,4-dione (10.3 mL, 0.1 mol) was diluted with AcOH and cooled to 0° C. NaNO$_2$ (6.9 g, 0.1 mol) was dissolved in H$_2$O (10 mL) and added dropwise, keeping the internal temperature ≦10° C. The mixture was stirred for 1 h with cooling then 3 h at room temperature. Ethyl acetoacetate (14 mL, 0.11 mol) was dissolved in 1:1 AcOH/H$_2$O (100 mL) and Zn powder (7.19 g, 0.11 mol) was added. To this the oxime solution was added and the mixture was heated at 100° C. for 30 min then poured into H$_2$O (0.8 L). The aqueous mixture was extracted with EtOAc (3×500 mL). The combined organic extracts were washed (brine), dried (MgSO$_4$), filtered, and evaporated in vacuo. The residue was purified by SiO$_2$ chromatography (heptane/EtOAc gradient elution) to afford 5-acetyl-2,4-dimethyl-1H-pyrrole-3-carboxylic acid ethyl ester (4.32 g). An aliquot (3.5 g, 16.7 mmol) was added to KOH (4.22 g, 75.3 mmol) dissolved in H$_2$O (5 mL) and the mixture was heated at 130° C. for 18 h. It was then cooled, diluted with H$_2$O (50 mL) and acidified with 2 M aq HCl. This mixture was extracted with EtOAc (3×50 mL). The combined organic extracts were washed (brine), dried (MgSO$_4$), filtered, and evaporated in vacuo. The residue was purified by SiO$_2$ chromatography (EtOAc) to afford 1-(3,5-dimethyl-1H-pyrrol-2-yl)-ethanone (1.05 g). An aliquot (536 mg, 3.9 mmol) was suspended in N,N-dimethylformamide dimethyl acetal (1.2 mL, 8.8 mmol) in a N$_2$-flushed flask and heated at 90° C. for 48 h. The mixture was cooled and triturated in cold EtOAc. The resulting precipitate was filtered and washed with EtOAc to afford the title compound (444 mg) as a buff. 1H-NMR (DMSO-d$_6$) δ: 1.41 (s, 3H, CH$_3$), 2.23 (s, 3H, CH$_3$), 2.23 (br. s, 6H, CH$_3$), 4.77 (d, 1H, J=12.4 Hz, CH), 4.95 (s, 1H, pyrrolyl-H), 6.85 (d, 1H, J=12.4 Hz, CH).

Example 8

[4-(3,5-Dimethyl-1H-pyrrol-2-yl)-pyrimidin-2-yl]-(4-fluoro-phenyl)-amine [45]

3-Dimethylamino-1-(3,5-dimethyl-1H-pyrrol-2-yl)-propenone (125 mg, 0.65 mmol), 4-fluorophenyl guanidine nitrate (211 mg, 0.98 mmol), and $K_2CO_3$ (149 mg, 1.08 mmol) were partially dissolved in 2-methoxyethanol and heated at 120° C. for 18 h. The mixture was concentrated in vacuo and purified by $SiO_2$ chromatography (5-g Isolute SI™ cartridge eluted with an heptane/EtOAc gradient). The crude product was triturated in $iPr_2O$ to afford the title compound (158 mg) as a buff solid. M.p. 168.4–171.5° C. MS: $[M+H]^+$=283.9 ($C_{16}H_{15}FN_4$ requires 282.3). $^1$H-NMR (CDCl$_3$) δ: 2.30 (s, 3H, CH$_3$), 2.35 (s, 3H, CH$_3$), 5.85 (s, 1H, pyrrolyl-H), 6.83 (d, 1H, J=5.6 Hz, pyrimidinyl-H), 6.87 (br. s, 1H, NH), 7.05 (t, 2H, J=8.5 Hz, Ph-H), 7.51–7.54 (m, 2H, Ph-H), 8.26 (d, 1H, J=5.4 Hz, pyrimidinyl-H), 9.08 (br. s, 1H, NH).

Example 9

3-Dimethylamino-1-(1,2,4-trimethyl-1H-pyrrol-3-yl)-propenone

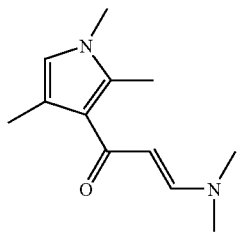

KOH (818 mg, 14.6 mmol) was partially dissolved in DMSO (115 mL) and stirred for 5 min. 1-(2,4-dimethyl-1H-pyrrol-3-yl)-ethanone (1 g, 7.3 mmol) was added in small portions and the mixture was stirred for 45 min. Iodomethane (0.54 mL, 8.75 mmol) was added dropwise at such a rate as to maintain the internal temperature ≦30° C. The mixture was stirred for a further 45 min then poured into $H_2O$ (50 mL) and extracted with $Et_2O$ (3×60 mL). The combined organic extracts were washed (brine), dried (MgSO$_4$), filtered, and evaporated in vacuo to afford 1-(1,2,4-trimethyl-1H-pyrrol-3-yl)-ethanone (1.06 g) as a pink solid. This was suspended in 1,1-bis-dimethylamino-3,3-dimethyl-butan-2-one (3.6 mL, 17.5 mmol) in a $N_2$-flushed flask and heated at 70° C. for 36 h. The mixture was evaporated in vacuo and the residue triturated in EtOAc. The titled compound (973 mg) was obtained as a reddish solid. $^1$H-NMR (DMSO-d$_6$) δ: 1.30 (s, 3H, CH$_3$), 1.51 (s, 3H, CH$_3$), 2.20 (br. s, 6H, CH$_3$), 2.66 (s, 3H, CH$_3$), 4.57 (d, 1H, J=12.5 Hz, CH), 5.53 (s, 1H, pyrrolyl-H), 6.72 (d, 1H, J=12.7 Hz, CH).

Example 10

(4-Fluoro-phenyl)-[4-(1,2,4-trimethyl-1H-pyrrol-3-yl)-pyrimidin-2-yl]-amine [46]

3-Dimethylamino-1-(1,2,4-trimethyl-1H-pyrrol-3-yl)-propenone (150 mg, 0.73 mmol), 4-fluorophenyl guanidine nitrate (189 mg, 0.87 mmol) and $K_2CO_3$ (144 mg, 1.04 mmol) were partially dissolved in 2-methoxyethanol (3 mL) and heated at 110° C. 36 h. The mixture was concentrated in vacuo and purified by $SiO_2$ chromatography (heptane/EtOAc gradient elution). The title compound (20 mg) was obtained as a brownish solid after recrystallisation from $iPr_2O$/heptane. M.p. 124.2–128.3° C. MS: $[M+H]^+$=298.4 ($C_{17}H_{17}FN_4$ requires 296.3). $^1$H-NMR (CDCl$_3$) δ: 2.21 (s, 3H, CH$_3$), 2.42 (s, 3H, CH$_3$), 3.51 (s, 3H, CH$_3$), 6.40 (s, 1H, pyrrolyl-H), 6.76 (d, 1H, J=5.4 Hz, pyrimidinyl-H), 7.01 (t, 2H, J=8.8 Hz, Ph-H), 7.58–7.61 (m, 2H, Ph-H), 7.70 (br. s, 1H, NH), 8.28 (d, 1H, J=5.6 Hz, pyrimidinyl-H).

Example 11

3-Dimethylamino-1-(2,4-dimethyl-5-nitro-1H-pyrrol-3-yl)-propenone

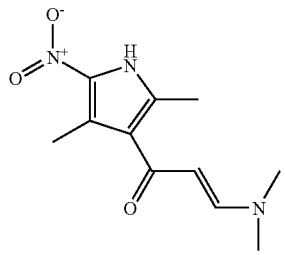

HNO$_3$ (0.28 mL of a 69% w/v aq solution, 4.37 mmol) was added dropwise to Ac$_2$O (5 mL) at room temperature, keeping the internal temperature ≦25° C. The nitrating mixture was stirred at room temperature for 15 min before cooling to –40° C. 1-(2,4-dimethyl-1H-pyrrol-3-yl)-ethanone (500 mg, 3.64 mmol) was dissolved in Ac$_2$O (6 mL) and added dropwise, keeping the internal temperature ≦–30° C. The mixture was stirred at –40° C. for 30 min then at –10° C. for a further 30 min. The mixture was poured into ice-water (50 mL) and was extracted with Et$_2$O (3×60 mL). The combined organic eztracts were washed (brine), dried (Na$_2$SO$_4$), filtered, and evaporated in vacuo to give a dark brown solid. This was recrystallised from MeOH to afford 1-(2,4-dimethyl-5-nitro-1H-pyrrol-3-yl)-ethanone (158 mg). An aliquot (150 mg, 0.82 mmol) was suspended in 1,1-bis-dimethylamino-3,3-dimethyl-butan-2-one (0.42 mL, 2.02 mmol) in a $N_2$-flushed flask and was heated at 70° C. for 18 h. The mixture was triturated in EtOAc to afford the title compound (119 mg) as a brown solid. $^1$H-NMR (DMSO-d$_6$) δ: 2.30 (s, 3H, CH$_3$), 2.40 (s, 3H, CH$_3$), 2.80 (br. s, 3H, CH$_3$), 3.07 (br. s, 3H, CH$_3$), 5.19 (d, 1H, J=12.7 Hz, CH), 7.45 (d, 1H, J=12.4 Hz, CH), 12.76 (br, 1H, NH).

Example 12

[4-(2,4-Dimethyl-5-nitro-1H-pyrrol-3-yl)-pyrimidin-2-yl]-(4-fluoro-phenyl)-amine [47]

3-Dimethylamino-1-(2,4-dimethyl-5-nitro-1H-pyrrol-3-yl)-propenone (110 mg, 0.46 mmol), 4-fluorophenyl guanidine nitrate (150 mg, 0.7 mmol), and $K_2CO_3$ (193 mg, 1.4 mmol) were partially dissolved in 2-methoxyethanol and heated at 120° C. for 18 h. The mixture was concentrated in vacuo and purified by $SiO_2$ chromatography (heptane/EtOAc gradient elution). The crude product was triturated in $iPr_2O$ to afford the title compound (22 mg) as a pale orange solid. M.p. 166.3–170.1° C. MS: $[M+H]^+$=329.3

($C_{16}H_{14}FN_5O_2$ requires 327.3). $^1$H-NMR (DMSO-$d_6$) δ: 2.49 (s, 3H, CH$_3$), 2.59 (s, 3H, CH$_3$), 6.73 (d, 1H, J=5.1 Hz, pyrimidinyl-H), 7.04 (t, 2H, J=8.8 Hz, Ph-H), 7.07 (br. s, 1H, NH), 7.55–7.58 (m, 2H, Ph-H), 8.44 (d, 1H, J=5.1 Hz, pyrimidinyl-H), 9.40 (br. s, 1H, NH).

The following compound was prepared in analogous manner:

N-[4-(2,4-Dimethyl-5-nitro-1H-pyrrol-3-yl)-pyrimidin-2-yl]-N',N'-dimethyl-benzene-1,4-diamine [48]

M.p. 265–268° C. MS: [M+H]$^+$=353.0 ($C_{18}H_{20}N_6O_2$ requires 352.4). $^1$H-NMR (DMSO-$d_6$) δ: 2.39 (s, 3H, CH$_3$), 2.48 (br. s, 6H, CH$_3$), 2.82 (s, 3H, CH$_3$), 6.69 (d, 2H, J=9.0 Hz, Ph-H), 6.74 (d, 1H, J=5.1 Hz, pyrimidinyl-H), 7.50 (d, 2H, J=9.0 Hz, Ph-H), 8.38 (d, 1H, J=5.1 Hz, pyrimidinyl-H), 9.18 (s, 1H, NH), 13.00 (br. s, 1H, NH).

Example 13

[4-(5-Amino-2,4-dimethyl-1H-pyrrol-3-yl)-pyrimidin-2-yl]-(4-fluoro-phenyl)-amine [49]

[4-(2,4-Dimethyl-5-nitro-1H-pyrrol-3-yl)-pyrimidin-2-yl]-(4-fluoro-phenyl)-amine (45 mg, 0.14 mmol) was dissolved in EtOH (3 mL) and 10% Pd(C) catalyst (10 mg) was added, followed by hydrazine hydrate (48 µL of a 55% w/w aq solution, 0.84 mmol). The mixture was heated at reflux for 18 h. The cooled mixture was filtered through a pad of Celite filter aid and the filtrate was evaporated in vacuo. The residue was purified by SiO$_2$ chromatography (20:1 EtOAc/2 M ammonia in MeOH) to afford the title compound (14 mg) as a yellow solid. M.p. 227–231° C. MS: [M+H]$^+$=397.8 ($C_{16}H_{16}FN_5$ requires 297.3). $^1$H-NMR (CDCl$_3$) δ: 1.98 (s, 3H, CH$_3$), 2.37 (s, 3H, CH$_3$), 4.86 (br. s, 2H, NH$_2$), 6.65 (d, 1H, J=4.9 Hz, pyrimidinyl-H), 7.03 (t, 2H, J=8.3 Hz, Ph-H), 7.49 (br. s, 2H, NH), 7.58–7.61 (m, 2H, Ph-H), 8.53 (d, 1H, J=4.9 Hz, pyrimidinyl-H).

Example 14

[4-(5-Bromo-2,4-dimethyl-1H-pyrrol-3-yl)-pyrimidin-2-yl]-(4-fluoro-phenyl)-amine [50]

[4-(2,4-Dimethyl-1H-pyrrol-3-yl)-pyrimidin-2-yl]-(4-fluoro-phenyl)-amine (80 mg, 0.28 mmol) was dissolved in THF (4 mL) and cooled to −50° C. N-Bromosuccinimide (55 mg, 0.31 mmol) was dissolved in THF (2 mL) and added dropwise, keeping the internal temperature ≦−40° C. The mixture was stirred for 1 h with cooling then evaporated in vacuo. The residue was treated with H$_2$O (10 mL) and extracted with EtOAc (3×10 mL). The combined organic extractss were washed (brine), dried (MgSO$_4$), filtered, and evaporated in vacuo. The crude product was purified by SiO$_2$ chromatography heptane/EtOAc gradient elution) to afford the title compound (19 mg) as an orange solid after recrystallisation from iPr$_2$O. M.p. 181.4–183.3° C. MS: [M+H]$^+$=362.9 ($C_{16}H_{14}BrFN_4$ requires 361.2). $^1$H-NMR (CDCl$_3$) δ: 2.10 (s, 3H, CH$_3$), 2.36 (s, 3H, CH$_3$) 6.56 (d, 1H, J=5.1 Hz, pyrimidinyl-H), 6.97 (t, 2H, J=8.3 Hz, Ph-H), 7.00 (br. s, 1H, NH), 7.79–7.52 (m, 2H, Ph-H), 8.85 (br. s, 1H, NH), 8.26 (d, 1H, J=5.1 Hz, pyrimidinyl-H).

The following compound was prepared in analogous manner:

[4-(5-Bromo-2,4-dimethyl-1H-pyrrol-3-yl)-pyrimidin-2-yl]-(3-nitro-phenyl)-amine [51]

M.p. 198.1–203° C. MS: [M+H]$^+$=389.3 ($C_{16}H_{14}BrN_5O_4$ requires 361.2). $^1$H-NMR (CDCl$_3$) δ: 2.49 (s, 3H, CH$_3$), 2.59 (s, 3H, CH$_3$) 6.73 (d, 1H, J=5.1 Hz, pyrimidinyl-H), 7.04 (t, 2H, J=8.8 Hz, Ph-H), 7.57 (m, 2H, Ph-H), 7.90 (br. s, 1H, NH), 8.44 (d, 1H, J=5.1 Hz, pyrimidinyl-H), 9.40 (br. s, 1H, NH).

Example 15

[4-(5-Chloro-2,4-dimethyl-1H-pyrrol-3-yl)-pyrimidin-2-yl]-(4-fluoro-phenyl)-amine [52]

[4-(2,4-Dimethyl-1H-pyrrol-3-yl)-pyrimidin-2-yl]-(4-fluoro-phenyl)-amine (80 mg, 0.28 mmol) was dissolved in THF (4 mL) and cooled to −60° C. N-Chlorosuccinimide (41 mg, 0.31 mmol) was dissolved in THF (2 mL) and added dropwise, keeping the internal temperature ≦−50° C. The mixture was stirred for 30 min with cooling then evaporated in vacuo. The residue was treated with H$_2$O (10 mL) and extracted with EtOAc (3×10 mL). The combined organic extracts were washed (brine), dried (MgSO$_4$), filtered, and evaporated in vacuo. The crude product was purified by SiO$_2$ chromatography (heptane/EtOAc gradient elution) to afford the title compound (37 mg) as an orange solid after recrystallisation from iPr$_2$O. M.p. 200–203° C. MS: [M+H]$^+$=317.7 ($C_{16}H_{14}ClFN_4$ requires 316.8). $^1$H-NMR (CDCl$_3$) δ: 2.17 (s, 3H, CH$_3$), 2.42 (s, 3H, CH$_3$) 6.77 (d, 1H, J=5.9 Hz, pyrimidinyl-H), 7.02–7.06 (m, 3H, Ph-h, NH), 7.54–7.56 (m, 2H, Ph-H), 7.95 (br. s, 1H, NH), 8.25 (d, 1H, J=5.4 Hz, pyrimidinyl-H).

Example 16

[4-(5-Diethylaminomethyl-2,4-dimethyl-1H-pyrrol-3-yl)-pyrimidin-2-yl]-(4-fluoro-phenyl)-amine [53]

Diethylamine (40 µL, 0.31 mmol) was diluted with methanol (0.5 mL) and formaldehyde (30 µL of a 37% w/w aq solution, 0.37 mmol) was added. [4-(2,4-Dimethyl-1H-pyrrol-3-yl)-pyrimidin-2-yl]-(4-fluoro-phenyl)-amine (87 mg, 0.31 mmol) was added in small portions and the mixture was heated to reflux. After 1.5 h the mixture was diluted with H$_2$O (10 mL). The resulting precipitate was filtered and triturated in 2 M aq HCl. The mixture was filtered and the filtrate was washed with 2 M aq NaOH. The filtrate was extracted with EtOAc (3×15 mL). The combined organic extracts were washed (brine), dried (MgSO$_4$), filtered, and evaporated in vacuo. The crude product was purified by SiO$_2$ chromatography (heptane/EtOAc gradient elution) to afford the title compound (36 mg) as an orange solid after recrystallisation from iPr$_2$O. M.p. 71.9–74.2° C. MS: [M+H]$^+$=367.7 ($C_{21}H_{26}FN_5$ requires 367.5). $^1$H-NMR (CD$_3$OD) δ: 1.10 (t, 6H, J=7.1 Hz, CH$_3$), 2.19 (s, 3H, CH$_3$), 2.41 (s, 3H, CH$_3$), 2.58 (t, 4H, J=7.8 Hz, CH$_2$), 3.56 (s, 2H, CH$_2$), 6.78 (d, 1H, J=5.6 Hz, pyrimidinyl-H), 7.00 (t, 2H, J=8.5 Hz, Ph-H), 7.61–7.63 (m, 2H, Ph-H), 8.22 (d, 1H, J=5.4 Hz, pyrimidinyl-H).

The following compounds were prepared in analogous manner:

[4-(5-Dimethylaminomethyl-2,4-dimethyl-1H-pyrrol-3-yl)-pyrimidin-2-yl]-(4-fluoro-phenyl)-amine [54]

M.p. 88.4–91.6° C. MS: [M+H]$^+$=340.6 ($C_{19}H_{22}FN_5$ requires 339.4). $^1$H-NMR (CDCl$_3$) δ: 2.18 (s, 3H, CH$_3$), 2.56 (s, 6H, CH$_3$), 2.42 (s, 3H, CH$_3$), 3.38 (s, 2H, CH$_2$), 6.75 (d, 1H, J=5.4 Hz, pyrimidinyl-H), 7.00 (t, 2H, J=8.6 Hz, Ph-H), 7.13 (br. s, 1H, NH), 7.56–7.59 (m, 2H, Ph-H), 8.31 (d, 1H, J=5.1 Hz, pyrimidinyl-H), 8.55 (br. s, 1H, NH).

[4-(2,4-Dimethyl-5-morpholin-4-ylmethyl-1H-pyrrol-3-yl)-pyrimidin-2-yl]-(4-fluoro-phenyl)-amine [55]

M.p. 94.7–97.6° C. MS: [M+H]$^+$=382.1 ($C_{21}H_{24}FN_5O$ requires 381.5). $^1$H-NMR (DMSO-d$_6$) δ: 2.12 (s, 3H, CH$_3$), 2.33–2.35 (m, 7H, CH$_3$, CH$_2$), 3.55 (m, 4H, CH$_2$), 4.03 (s, 2H, CH$_2$), 6.73 (d, 1H, J=5.4 Hz, pyrimidinyl-H), 7.08 (t, 2H, J=9.0 Hz, Ph-H), 7.74–7.78 (m, 2H, Ph-H), 8.28 (d, 1H, J=5.4 Hz, pyrimidinyl-H), 9.27 (s, 1H, NH), 10.76 (s, 1H, NH).

{4-[2,4-Dimethyl-5-(4-methyl-piperazin-1-ylmethyl)-1H-pyrrol-3-yl]-pyrimidin-2-yl}-(4-fluorophenyl)-amine [56]

M.p. 120.4–123.1° C. MS: [M+H]$^+$=396.4 ($C_{22}H_{27}FN_5$ requires 394.5). $^1$H-NMR (CDCl$_3$) δ: 1.62 (br. s, 4H, CH$_2$), 2.10 (s, 3H, CH$_3$), 2.34 (s, 3H, CH$_3$), 2.37 (s, 3H, CH$_3$), 2.43 (br. s, 4H, CH$_2$), 3.42 (s, 2H, CH$_2$), 6.67 (d, 1H, J=5.4 Hz, pyrimidinyl-H), 6.91–6.96 (m, 3H, Ph-H, NH), 7.50–7.52 (m, 2H, Ph-H), 8.24 (d, 1H, J=5.4 Hz, pyrimidinyl-H), 8.30 (br. s, 1H, NH).

Example 17

Kinase Specificity of Selected Compound

Selected compounds from the above examples were investigated for their kinase selectivity. A panel of protein kinases, including the CDKs relevant to the present invention, as well as a representative number of functionally unrelated kinases, were used.

Assays for CDK4/Cyclin D1, CDK2/Cyclin E, CDIK1/Cyclin B kinase may be carried out by monitoring phosphorylation of GST-Rb in an appropriate system. Thus, GST-Rb phosphorylation, induced by CDK4/Cyclin D1, CDK2/Cyclin E or CDK1/Cyclin B is determined by incorporation of radio-labeled phosphate in GST-Rb (772–928) using radiolabelled ATP in 96-well format in vitro kinase assay. The phosphorylation reaction mixture (total volume 40 μl) consisted of 50 mM HEPES pH 7.4, 20 mM MgCl$_2$, 5 mM EGTA, 2 mM DTT, 20 mM β-glycerophosphate, 2 mM NaF, 1 mM Na$_3$VO$_4$, Protease Inhibitors Cocktail (Sigma, see above), BSA 0.5 mg/ml, 1 μg purified enzyme complex, 10 μl of GST-Rb-Sepharose beads, 100 μM ATP, 0.2 μCi $^{32}$P-ATP. The reaction is carried out for 30 min at 30° C. at constant shaking. At the end of this period 100 μl of 50 mM HEPES, pH 7.4 and 1 mM ATP is added to each well and the total volume transferred onto GFC filtered plate. The plate is washed 5 times with 200 μl of 50 mM HEPES, pH 7.4 and 1 mM ATP. To each well were added 50 μl scintillant liquid and the radioactivity of the samples is measured on Scintilation counter (Topcount, HP). The IC50 values of different peptides were calculated using GraFit software.

Alternatively, CDK2/cyclin A kinase assays may be performed in 96-well plates using recombinant CDK2/cyclin A. Assay buffer consisted of 25 mM β-glycerophosphate, 20 mM MOPS, 5 mM EGTA, 1 mM DTT, 1 mM NaVO$_3$, pH 7.4, into which is added 2–4 μg of CDK2/cyclin A with substrate pRb (773–928). The reaction is initiated by addition of Mg/ATP mix (15 mM MgCl$_2$, 100 μM ATP with 30–50 kBq per well of [γ-$^{32}$P]-ATP) and mixtures incubated for 10–30 min, as required, at 30° C. Reactions were stopped on ice, followed by filtration through p81 filterplates (Whatman Polyfiltronics, Kent, UK). After washing 3 times with 75 mM orthophosphoric acid, plates were dried, scintillant added and incorporated radioactivity measured in a scintillation counter (TopCount, Packard Instruments, Pangbourne, Berks, UK).

PKCα kinase activity may be measured by the incorporation of radio-labeled phosphate in Histone 3, as described. The reaction mixture (total volume 65 μl) consist of 50 mM Tris-HCl, 1 mM Calcium acetate, 3 mM DTT, 0.03 mg/ml Phosphatidylserine, 2.4 μg/ml PMA, 0.04% NP40, 12 mM Mg/Cl, purified PKCα-100 ng, Histone 3, 0.2 mg/ml, 100 μM ATP, 0.2 μCi [γ-$^{32}$P]-ATP. The reaction is carried over 15 min at 37° C. in microplate shaker and is stopped by adding 10 μl 75 mM orthophosphoric acid and placing the plate on ice. 50 μl of the reaction mixture is transferred onto P81 filterplate and after washing off the free radioactive phosphate (3 times with 200 μl 75 mM orthophosphoric acid per well) 50 μl of scintillation liquid (Microscint 40) were added to each well and the radioactivity is measured on Scintillation counter (Topcount, HP).

For use in said assays CDK2 and/or PKC may be obtained from available sources or produced by recombinant methods as described. His-tagged CDK2/Cyclin E and CDK1/Cyclin B may be co-expressed and PKCα singularly expressed in Sf 9 insect cells infected with the appropriate baculovirus constructs. The cells are harvested two days after infection by low speed centrifugation and the proteins purified from the insect cell pellets by Metal-chelate chromatography. Briefly, the insect cell pellet is lysed in Buffer A (10 mM Tris-HCl, pH 8.0, 150 mM NaCl, 0.02% NP40 and 5 mM β-marcaptoethanol, 1 mM NaF. 1 mM Na$_3$VO$_4$ and Protease Inhibitors Coctail (Sigma) containing AEBSF, pepstatin A, E 64, bestatin, leupeptin) by sonication. The soluble fraction is cleared by centrifugation and loaded onto Ni-NTA-Agarose (Quiagen). Non bound proteins were washed off with 300 mM NaCl, 5–15 mM Imidazole in Buffer A and the bound proteins eluted with 250 mM Imidazole in Buffer A. The purified proteins are extensively dialyzed against Storage buffer (20 mM HEPES pH 7.4, 50 mM NaCl, 2 mM DTT, 1 mM EDTA, 1 mM EGTA, 0.02% NP40, 10% v/v Glycerol) aliquoted and stored at –70° C. PKC-α-6×His may be purified the same way but using different buffers-50 mM NaH2PO4, pH 8.0 and 0.05% Triton X-100 instead of Tris and NP40 respectively.

The results in the Table 1 below show that the compounds in question exhibit a high degree of selectivity for inhibition of CDKs.

TABLE 1

| Compound | CDK2/cyclin E (IC$_{50}$, μM) |
|---|---|
| 1 | 1.0 ± 0.7 |
| 2 | 0.04 |
| 3 | 0.5 |
| 4 | 1.3 ± 0.4 |
| 5 | 1.7 |
| 6 | 1.3 |
| 7 | 2.9 |
| 8 | 1.4 |
| 12 | 0.90 |

TABLE 1-continued

| Compound | CDK2/cyclin E (IC$_{50}$, µM) |
|---|---|
| 16 | 1.52 |
| 17 | 1.73 |
| 31 | 0.03 |
| 32 | 0.09 |
| 33 | 0.09 |
| 34 | 0.18 |
| 35 | 0.55 |
| 36 | 0.04 |
| 37 | 0.39 |
| 38 | 0.86 |
| 39 | 1.02 |

TABLE 1-continued

| Compound | CDK2/cyclin E (IC$_{50}$, µM) |
|---|---|
| 40 | 0.15 |
| 41 | 0.05 |
| 42 | 0.76 |
| 43 | 0.54 |
| 44 | 0.22 |
| 46 | 1.79 |
| 47 | 0.06 |
| 48 | 0.96 |
| 50 | 0.55 |
| 51 | 0.37 |
| 52 | 0.73 |
| 53 | 0.87 |
| 54 | 0.14 |
| 55 | 0.87 |
| 56 | 1.51 |

Example 18

Anti-proliferative Effect of Selected Compounds

Selected compounds from the above examples were subjected to a standard cellular proliferation assay using a range of different human tumour cell lines. Standard 72-h MTT (thiazolyl blue; 3-[4,5-dimethylthiazol-2-yl]-2,5-diphenyltetrazolium bromide) assays were performed (Haselsberger, K.; Peterson, D. C.; Thomas, D. G.; Darling, J. L. Anti Cancer Drugs 1996, 7, 331–8; Loveland, B. E.; Johns, T. G.; Mackay, I. R.; Vaillant, F.; Wang, Z. X.; Hertzog, P. J. Biochemistry International 1992, 27, 501–10). Human tumour cell lines were obtained from the ATCC (American Type Culture Collection, 10801 University Boulevard, Manessas, Va. 20110-2209, USA).

The results in Table 2 below illustrate the anti-proliferative effect of compounds described in this application.

TABLE 2

| | Cytotoxicity (IC$_{50}$, µM) | | | | | | | |
|---|---|---|---|---|---|---|---|---|
| | Human tumour cell line | | | | | Non-transformed cell line | | |
| Compound | A549 | HeLa | HT29 | MCF7 | Saos-2 | Hs27 | IMR90 | WI38 |
| 2 | 3.30 | | 3.30 | | 6.60 | | | |
| 12 | 15.00 | | 3.10 | | 17.00 | | | |
| 16 | 4.39 | | | | | | | |
| 31 | 0.40 | 0.26 | 0.31 | 0.26 | 0.74 | 18.9 | 14.1 | 9.7 |
| 32 | 2.47 | 1.38 | 2.41 | 1.93 | 2.89 | 15.1 | 20.8 | 9.6 |
| 33 | 0.88 | 0.76 | 1.83 | 1.03 | 0.89 | 4.2 | 14.1 | 9.9 |
| 34 | 3.64 | | 0.95 | | 3.40 | | | |
| 35 | 0.51 | 0.09 | 0.11 | 0.45 | 0.75 | 35.1 | 37.3 | 21.3 |
| 36 | 1.12 | | 2.56 | | 0.90 | | | |
| 37 | 0.47 | | 0.28 | | 1.04 | | | |
| 38 | 3.60 | | 0.72 | | 3.12 | | | |
| 39 | 4.37 | | 3.27 | | 5.88 | | | |
| 40 | 0.86 | | 1.47 | | 1.13 | | | |
| 41 | 2.95 | | 2.11 | | 5.80 | | | |
| 42 | 1.49 | | 0.28 | | 2.23 | | | |
| 43 | 1.41 | | 0.17 | | 1.50 | | | |
| 44 | 1.36 | | 1.92 | | 2.61 | | | |
| 47 | 3.13 | | 3.11 | | 3.78 | | | |
| 48 | 3.05 | | 0.61 | | 2.65 | | | |
| 51 | 7.56 | | 2.92 | | 12.40 | | | |
| 53 | 0.97 | | 1.31 | | 1.61 | | | |
| 54 | 2.76 | | 3.20 | | 0.70 | | | |
| 56 | 13.80 | | 5.09 | | 14.15 | | | |

The invention claimed is:

1. A compound of general formula I:

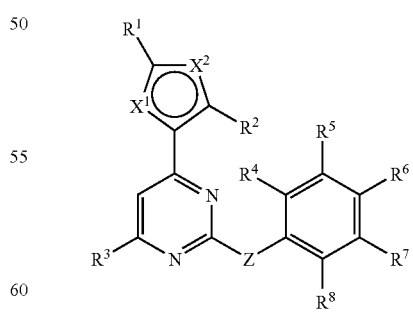

I wherein:

X$^1$ is CR$^9$;

X$^2$ is NR$^{10}$;

Z is NH;

33

R$^1$, R$^2$, R$^3$, R$^9$ and R$^{10}$ are independently H, alkyl, aryl, aralkyl, heterocycle, halogeno, NO$_2$, CN, OH, alkoxy, aryloxy, (R''')nNH$_2$, (R''')nNH—R', (R''')nN—(R')(R''), NH-aryl, N-(aryl)$_2$, COOH, COO—R', COO-aryl, CONH$_2$, CONH—R', CON—(R')(R''), CONH-aryl, CON-(aryl)$_2$, SO$_3$H, SO$_2$NH$_2$, CF$_3$, CO—R', or CO-aryl, wherein alkyl, aryl, aralkyl and heterocycle groups may be further substituted with one or more groups selected from halogen, NO$_2$, CN, OH, O-methyl, NH$_2$, COOH, CONH$_2$ and CF$_3$;

R$^4$, R$^5$, R$^7$, and R$^8$ are independently from each other H, substituted or unsubstituted lower alkyl, halogeno, NO$_2$, CN, OH, substituted or unsubstituted alkoxy, NH$_2$, NH—R', N—(R')(R''), COOH, COO—R', CONH$_2$, CONH—R', CON—(R')(R''), SO$_3$H, SO$_2$NH$_2$, or CF$_3$;

R$_6$ is H, substituted or unsubstituted lower alkyl, halogeno, NO$_2$, CN, OH, substituted or unsubstituted alkoxy, NH$_2$, NH—R', N—(R')(R''), COOH, COO—R', SO$_3$H, SO$_2$NH$_2$, or CF$_3$;

wherein R'R'' and R''' are each independently alkyl groups that may be the same or different and n is 0 or 1; and wherein at least two or three of R$^1$, R$_2$ and R$_9$ are not hydrogen; or a pharmaceutically acceptable salts thereof.

2. A compound according to claim 1, wherein;

R$^1$, R$^2$, R$^3$ and R$^9$ are each independently selected from H, alkyl, aryl, aralkyl, heterocycle, halogeno, NO$_2$, CN, OH, alkoxy, aryloxy, (R''')nNH$_2$, (R''')nNH—R', (R''')nN—(R')(R''), COOH, COO—R', CONH$_2$, CONH—R', CON—(R')(R''), SO$_3$H, SO$_2$NH$_2$, CF$_3$, and CO—R' wherein alkyl, aryl and aralkyl groups may be further substituted with one or more groups selected from halogeno, NO$_2$, CN, OH, O-methyl, NH$_2$, COOH, CONH$_2$ and CF$_3$.

3. A compound according to claim 1, wherein said compound is selected from 2-[N-(phenyl)]-4-(2,4-dimethylpyrrol-3-yl)pyrimidineamines in which the phenyl group is 2-, 3-, 4-or 5-substituted by at least one of F, NH$_2$, NO$_2$, OH, Cl, Br, I, CN, CH$_2$OH, CF$_3$ or OMe.

4. A compound according to claim 3, wherein the phenyl group is mono-substituted by F, NH$_2$, NO$_2$, OH, Cl, Br, I, CH$_2$OH, CN, CF$_3$ or OMe at any of the 2,3,4 or 5-positions, or di-substituted by 2,4-difluoro, 3,5-difluoro, 3,4-difluoro, 2,4-dichloro, 3,5-dichloro, 3,4-dichloro or 4-chloro-3-trifluoromethyl.

5. A compound according to claim 1, wherein said compound is selected from 2-[N-(phenyl)]-4-(3,5-dimethyl-1H-pyrrole-2-carbonitrile)pyrimidineamines in which the phenyl group is 2-, 3- or 4-substituted by at least one of F, NH(CH$_3$)$_2$, NO$_2$, OH, Cl, Br, I or CF$_3$.

6. A compound according to claim 5, wherein the phenyl group is mono-substituted by F, NH(CH$_3$)$_2$, NO$_2$, OH, I or CF$_3$ at any of the 3 or 4-positions, or di-substituted by 4-methyl-3-nitro, 3-iodo-4-methyl, 4-chloro-3-methyl, 3-hydroxy-4-methyl, 4-fluoro-3-methyl or 4-methyl-3-fluoro.

7. A compound according to claim 1, wherein said compound is selected from 2-[N-(phenyl)]-4-(2,4-dimethyl-5-nitro-1H-pyrrol-3-yl)-pyrimidinamines wherein the phenyl group is mono-substituted by F, NIH(CH$_3$)$_2$, NO$_2$, OH, I or CF$_3$ at the 4-position.

8. A compound according to claim 7, wherein the phenyl group is substituted by a fluoro or NH(CH$_3$)$_2$ group.

9. A compound according to claim 1, wherein said compound is selected from 2-[N-(phenyl)]-4-(2,4-dimethyl-5-halogeno-1H-pyrrol-3-yl)-pyrimidinamines wherein the

34 phenyl group is mono-substituted by F, NH(CH$_3$)$_2$, NO$_2$, OH, I or CF$_3$ at the 3 or 4-positions.

10. A compound according to claim 9, wherein the phenyl group is substituted by a 4-fluoro or 3-nitro group, the halogeno group being chloro or bromo.

11. A compound according to claim 1, selected from 2-[N-(phenyl)]-4-(2,4-dimethyl-5-dialkylaminoalkyl-1H-pyrrol-3-yl)-pyrimidinamines wherein the phenyl group is mono-substituted by F, NH(CH$_3$)$_2$, NO$_2$, OH, I or CF$_3$ at the 4-position.

12. A compound according to claim 11, wherein the phenyl group is substituted by fluoro, and the dialkylaminoalkyl group is diethylaminomethyl or dimethylaminomethyl.

13. A compound according to claim 1, selected from 2-[N-(phenyl)]-4-(2,4-dimethyl-5-(heterocycle)-1H-pyrrol-3-yl)-pyrimidinamines wherein the phenyl group is mono-substituted by F, NH(CH$_3$)$_2$, NO$_2$, OH, I or CF$_3$ at the 4-position.

14. A compound according to claim 13, wherein the phenyl group is substituted by fluoro, and the heterocycle group is 5-morpholin-4-ylmethyl or 4-methyl-piperazin-1-ylmethyl.

15. A compound selected from:

[4-(2,4-Dimethyl-1H-pyrrol-3-yl)-pyrimidin-2-yl]-(4-fluoro-phenyl)-amine;

[4-(2,4-Dimethyl-1H-pyrrol-3-yl)-pyrimidin-2-yl]-(3-nitro-phenyl)-amine;

[4-(2,4-Dimethyl-1H-pyrrol-3-yl)-pyrimidin-2-yl]-(4-iodo-phenyl)-amine;

(3,4-Difluoro-phenyl)-[4-(2,4-dimethyl-1H-pyrrol-3-yl)-pyrimidin-2-yl]-amine;

(4-Chloro-phenyl)-[4-(2,4-dimethyl-1H-pyrrol-3-yl)-pyrimidin-2-yl]-amine;

(3,5-Difluoro-phenyl)-[4-(2,4-dimethyl-1H-pyrrol-3-yl)-pyrimidin-2-yl]-amine;

4-[4-(2,4-Dimethyl-1H-pyrrol-3-yl)-pyrimidin-2-ylamino]-phenol;

3-[4-(2,4-Dimethyl-1H-pyrrol-3-yl)-pyrimidin-2-ylamino]-phenol;

(2,4-Difluoro-phenyl)-[4-(2,4-dimethyl-1H-pyrrol-3-yl)-pyrimidin-2-yl]-amine;

(2,4-Dichloro-phenyl)-[4-(2,4-dimethyl-1H-pyrrol-3-yl)-pyrimidin-2-yl]-amine;

(4-Chloro-3-trifluoromethyl-phenyl)-[4-(2,4-dimethyl-1H-pyrrol-3-yl)-pyrimidin-2-yl]-amine;

[4-(2,4-Dimethyl-1H-pyrrol-3-yl)-pyrimidin-2-yl]-(4-trifluoromethyl-phenyl)-amine;

[4-(2,4-Dimethyl-1H-pyrrol-3-yl)-pyrimidin-2-yl]-(3-trifluoromethyl-phenyl)-amine;

(3-Chloro-phenyl)-[4-(2,4-dimethyl-1H-pyrrol-3-yl)-pyrimidin-2-yl]-amine;

N-[4-(2,4-Dimethyl-1H-pyrrol-3-yl)-pyrimidin-2-yl]-N',N'-dimethyl-benzene-1,4-diamine;

(3-Chloro-4-iodo-phenyl)-[4-(2,4-dimethyl-1H-pyrrol-3-yl)-pyrimidin-2-yl]-amine;

[4-(2,4-Dimethyl-1H-pyrrol-3-yl)-pyrimidin-2-yl]-(3-fluoro-4-iodo-phenyl)-amine;

3,5-Dimethyl-4-[2-(3-nitro-phenylamino)-pyrimidin-4-yl]-1H-pyrrole-2-carbonitrile;

4-[2-(4-Fluoro-phenylamino)-pyrimidin-4-yl]-3,5-dimethyl-1H-pyrrole-2-carbonitrile;

4-[2-(4-Hydroxy-phenylamino)-pyrimidin-4-yl]-3,5-dimethyl-1H-pyrrole-2-carbonitrile;

3,5-Dimethyl-4-[2-(4-trifluoromethyl-phenylamino)-pyrimidin-4-yl]-1H-pyrrole-2-carbonitrile;

4-[2-(4-Iodo-phenylamino)-pyrimidin-4-yl]-3,5-dimethyl-1H-pyrrole-2-carbonitrile;
4-[2-(3-Hydroxy-phenylamino)-pyrimidin-4-yl]-3,5-dimethyl-1H-pyrrole-2-carbonitrile;
3,5-Dimethyl-4-[2-(4-methyl-3-nitro-phenylamino)-pyrimidin-4-yl]-1H-pyrrole-2-carbonitrile;
4-[2-(3-Iodo-4-methyl-phenylamino)-pyrimidin-4-yl]-3,5-dimethyl-1H-pyrrole-2-carbonitrile;
4-[2-(4-Chloro-3-methyl-phenylamino)-pyrimidin-4-yl]-3,5-dimethyl-1H-pyrrole-2-carbonitrile;
4-[2-(3-Hydroxy-4-methyl-phenylamino)-pyrimidin-4-yl]-3,5-dimethyl-1H-pyrrole-2-carbonitrile;
4-[2-(4-Fluoro-3-methyl-phenylamino)-pyrimidin-4-y1]-3,5-dimethyl-1H-pyrrole-2-carbonitrile;
4-[2-(3-Fluoro-4-methyl-phenylamino)-pyrimidin-4-yl]-3,5-dimethyl-1H-pyrrole-2-carbonitrile;
4-[2-(4-Dimethylamino-phenylamino)-pyrimidin-4-yl]-3,5-dimethyl-1H-pyrrole-2-carbonitrile;
4-[2-(4-Fluoro-phenylamino)-pyrimidin-4-yl]-3,5-dimethyl-1H-pyrrole-2-carboxylic acid amide;
[4-(3,5-Dimethyl-1H-pyrrol-2-yl)-pyrimidin-2-yl]-(4-fluoro-phenyl)-amine;
(4-Fluoro-phenyl)-[4-(1,2,4-trimethyl-1H-pyrrol-3-yl)-pyrimidin-2-yl]-amine;
[4-(2,4-Dimethyl-5-nitro-1H-pyrrol-3-yl)-pyrimidin-2-yl]-(4-fluoro-phenyl)-amine;
N-[4-(2,4-Dimethyl-5-nitro-1H-pyrrol-3-yl)-pyrimidin-2-yl]-N',Nt-dimethyl-benzene-1,4-diamine;
[4-(5-Amino-2,4-dimethyl-1H-pyrrol-3-yl)-pyrimidin-2-yl]-(4-fluoro-phenyl)-amine;
[4-(5-Bromo-2,4-dimethyl-1H-pyrrol-3-yl)-pyrimidin-2-yl]-(4-fluoro-phenyl)-amine;
[4-(5-Bromo-2,4-dimethyl-1H-pyrrol-3-yl)-pyrimidin-2-yl]-(3-nitro-phenyl)-amine;
[4(5-Chloro-2,4-dimethyl-1H-pyrrol-3-yl)-pyrimidin-2-yl]-(4-fluoro-phenyl)-amine;
[4-(5-Diethylaminomethyl-2,4-dimethyl-1H-pyrrol-3-yl)-pyrimidin-2-yl]-(4-fluoro-phenyl)-amine;
[4-(5-Dimethylaminomethyl-2,4-dimethyl-1H-pyrrol-3-yl)-pyrimidin-2-yl]-(4-fluoro-phenyl)-amine;
[4-(2,4-Dimethyl-5-morpholin-4-ylmethyl-1H-pyrrol-3-yl)-pyrimidin-2-yl]-(4-fluoro-phenyl)-amine; and
{4-[2,4-Dimethyl-5-(4-methyl-piperazin-1-ylmethyl)-1H-pyrrol-3-yl)-pyrimidin-2-yl}-(4-fluoro-phenyl)-amine.

16. A compound according to claim 15 selected from;
[4-(2,4-Dimethyl-1H-pyrrol-3-yl)-pyrimidin-2-yl]-(4-fluoro-phenyl)-amine;
[4-(2,4-Dimethyl-1H-pyrrol-3-yl)-pyrimidin-2-yl]-(3-nitro-phenyl)-amine;
[4-(2,4-Dimethyl-1H-pyrrol-3-yl)-pyrimidin-2-yl]-(4-iodo-phenyl)-amine;
(3,4-Difluoro-phenyl)-[4-(2,4-dimethyl-1H-pyrrol-3-yl)-pyrimidin-2-yl]-amine;
(4-Chloro-phenyl)-[4-(2,4-dimethyl-1H-pyrrol-3-yl)-pyrimidin-2-yl]-amine;
(3,5-Difluoro-phenyl)-[4-(2,4-dimethyl-1H-pyrrol-3-yl)-pyrimidin-2-yl]-amine;
4-[4-(2,4-Dimethyl-1H-pyrrol-3-yl)-pyrimidin-2-ylamino]-phenol;
3-[4-(2,4-Dimethyl-1H-pyrrol-3-yl)-pyrimidin-2-ylamino]-phenol;
[4-(2,4-Dimethyl-1H-pyrrol-3-yl)-pyrimidin-2-yl]-(4-trifluoromethyl-phenyl)-amine;
(3-Chloro-4-iodo-phenyl)-4-(2,4-dimethyl-1H-pyrrol-3-yl)-pyrimidin-2-yl]-amine;
[4-(2,4-Dimethyl-1H-pyrrol-3-yl)-pyrimidin-2-yl]-(3-fluoro-4-iodo-phenyl)-amine;
3,5-Dimethyl-4-[2-(3-nitro-phenylamino)-pyrimidin-4-yl]-1H-pyrrole-2-carbonitrile;
4-[2-(4-Fluoro-phenylamino)-pyrimidin-4-yl]-3,5-dimethyl-1H-pyrrole-2-carbonitrile;
4-[2-(4-Hydroxy-phenylamino)-pyrimidin-4-yl]-3,5-dimethyl-1H-pyrrole-2-carbonitrile;
3,5-Dimethyl-4-[2-(4-trifluoromethyl-phenylamino)-pyrimidin-4-yl]-1H-pyrrole-2-carbonitrile;
4-[2-(4-Iodo-phenylamino)-pyrimidin-4-yl]-3,5-dimethyl-1H-pyrrole-2-carbonitrile;
4-[2-(3-Hydroxy-phenylamino)-pyrimidin-4-yl]-3,5-dimethyl-1H-pyrrole-2-carbonitrile;
3,5-Dimethyl-4-[2-(4-methyl-3-nitro-phenylamino)-pyrimidin-4-yl]-1H-pyrrole-2-carbonitrile;
4-[2-(3-Iodo-4-methyl-phenylamino)-pyrimidin-4-yl]-3,5-dimethyl-1H-pyrrole-2-carbonitrile;
4-[2-(4-Chloro-3-methyl-phenylamino)-pyrimidin-4-yl]-3,5-dimethyl-1H-pyrrole-2-carbonitrile;
4-[2-(3-Hydroxy-4-methyl-phenylamino)-pyrimidin-4-yl]-3,5-dimethyl-1H-pyrrole-2-carbonitrile;
4-[2-(4-Fluoro-3-methyl-phenylamino)-pyrimidin-4-yl]-3,5-dimethyl-1H-pyrrole-2carbonitrile;
4-[2-(3-Fluoro-4-methyl-phenylamino)-pyrimidin-4-yl]-3,5-dimethyl-1H-pyrrole-2carbonitrile;
4-[2-(4-Dimethylamino-phenylamino)-pyrimidin-4-yl]-3,5-dimethyl-1H-pyrrole-2-carbonitrile;
4-[2-(4-Fluoro-phenylamino)-pyrimidin-4-yl]-3,5-dimethyl-1H-pyrrole-2-carboxylic acid amide;
(4-Fluoro-phenyl)-[4-(1,2,4-trimethyl-1H-pyrrol-3-yl)-pyrimidin-2-yl]-amine;
[4-(2,4-Dimethyl-5-nitro-1H-pyrrol-3-yl)-pyrimidin-2-yl]-(4-fluoro-phenyl)-amine;
N-[4-(2,4-Dimethyl-5-nitro-1H-pyrrol-3-yl)-pyrimidin-2-yl]-N',N'-dimethyl-benzene-1,4-diamine;
[4-(5-Bromo-2,4-dimethyl-1H-pyrrol-3-yl)-pyrimidin-2-yl]-(4-fluoro-phenyl)-amine;
[4- (5-Bromo-2,4-dimethyl- lH-pyrrol-3-yl)-pyrimidin-2-yl]-(3-nitro-phenyl)-amine;
[4-(5-Chloro-2,4-dimethyl-1H-pyrrol-3-yl)-pyrimidin-2-yl]-(4-fluoro-phenyl)-amine;
[4-(5-Diethylaminomethyl-2,4-dimethyl-1H-pyrrol-3-yl)-pyrimidin-2-yl]-(4-fluoro-phenyl)-amine;
[4-(5-Dimethylaminomethyl-2,4-dimethyl-1H-pyrrol-3-yl)-pyrimidin-2-yl]-(4-fluoro-phenyl)-amine;
[4-(2,4-Dimethyl-5-morpholin-4-ylmethyl-1H-pyrrol-3-yl)-pyrimidin-2-yl]-(4-fluoro-phenyl)-amine, and
{4-[2,4-Dimethyl-5-(4-methyl-piperazin-1-ylmethyl)-1H-pyrrol-3-yl)-pyrimidin-2-yl}-(4-fluoro-phenyl)-amine.

17. A compound according to claim 16 selected from;
[4-(2,4-Dimethyl-1H-pyrrol-3-yl)-pyrimidin-2-yl]-(4-fluoro-phenyl)-amine;
[4-(2,4-Dimethyl-1H-pyrrol-3-yl)-pyrimidin-2-yl]-(3-nitro-phenyl)-amine;
[4-(2,4-Dimethyl-1H-pyrrol-3-yl)-pyrimidin-2-yl]-(4-iodo-phenyl)-amine;
[4-(2,4-Dimethyl-1H-pyrrol-3-yl)-pyrimidin-2-yl]-(4-trifluoromethyl-phenyl)-amine;
3,5-Dimethyl-4-[2-(3-nitro-phenylamino)-pyrimidin-4-yl]-1H-pyrrole-2-carbonitrile;
4-[2-(4-Fluoro-phenylamino)-pyrimidin-4-yl]-3,5-dimethyl-1H-pyrrole-2-carbonitrile;
4-[2-(4-Hydroxy-phenylamino)-pyrimidin-4-yl]-3,5-dimethyl-1H-pyrrole-2-carbonitrile;

3,5-Dimethyl-4-[2-(4-trifluoromethyl-phenylamino)-pyrimidin-4-yl]-1H-pyrrole-2-carbonitrile;
4-[2-(4-Iodo-phenylamino)-pyrimidin-4-yl]-3,5-dimethyl-1H-pyrrole-2-carbonitrile;
4-[2-(3-Hydroxy-phenylamino)-pyrimidin-4-yl]-3,5-dimethyl-1H-pyrrole-2-carbonitrile;
3,5-Dimethyl-4-[2-(4-methyl-3-nitro-phenylamino)-pyrimidin-4-yl]-1H-pyrrole-2-carbonitrile;
4-[2-(3-Iodo-4-methyl-phenylamino)-pyrimidin-4-yl]-3,5-dimethyl-1H-pyrrole-2-carbonitrile;
4-[2-(4-Chloro-3-methyl-phenylamino)-pyrimidin-4-yl]-3,5-dimethyl-1H-pyrrole-2-carbonitrile;
4-[2-(3-Hydroxy-4-methyl-phenylamino)-pyrimidin-4-yl]-3,5-dimethyl-1H-pyrrole-2-carbonitrile;
4-[2-(4-Fluoro-3-methyl-phenylamino)-pyrimidin-4-yl]-3,5-dimethyl-1H-pyrrole-2-carbonitrile;
4-[2-(3-Fluoro-4-methyl-phenylamino)-pyrimidin-4-yl]-3,5-dimethyl-1H-pyrrole-2-carbonitrile;
4-[2-(4-Dimethylamino-phenylamino)-pyrimidin-4-yl]-3,5-dimethyl-1H-pyrrole-2-carbonitrile;
4-[2-(4-Fluoro-phenylamino)-pyrimidin-4-yl]-3,5-dimethyl-1H-pyrrole-2-carboxylic acid amide;
[4-(2,4-Dimethyl-5-nitro-1H-pyrrol-3-yl)-pyrimidin-2-yl]-(4-fluoro-phenyl)-amine;
N-[4-(2,4-Dimethyl-5-nitro-1H-pyrrol-3-yl)-pyrimidin-2-yl]-N',N"-dimethyl-benzene-1,4-diamine;
[4-(5-Bromo-2,4-dimethyl-1H-pyrrol-3-yl)-pyrimidin-2-yl]-(4-fluoro-phenyl)-amine;
[4-(5-Bromo-2,4-dimethyl-1H-pyrrol-3-yl)-pyrimidin-2-yl]-(3-nitro-phenyl)-amine;
[4-(5-Chloro-2,4-dimethyl-1H-pyrrol-3-yl)-pyrimidin-2-yl]-(4-fluoro-phenyl)-amine;
[4-(5-Diethylaminomethyl-2,4-dimethyl-1H-pyrrol-3-yl)-pyrimidin-2-yl]-(4-fluoro-phenyl)-amine;
[4-(5-Dimethylaminomethyl-2,4-dimethyl-1H-pyrrol-3-yl)-pyrimidin-2-yl]-(4-fluoro-phenyl)-amine, and
[4-(2,4-Dimethyl-5-morpholin-4-ylmethyl-1H-pyrrol-3-yl)-pyrimidin-2-yl]-(4-fluoro-phenyl)-amine.

18. A compound according to claim 17 selected from;
[4-(2,4-Dimethyl-1H-pyrrol-3-yl)-pyrimidin-2-yl]-(3-nitro-phenyl)-amine;
[4-(2,4-Dimethyl-1H-pyrrol-3-yl)-pyrimidin-2-yl]-(4-iodo-phenyl)-amine;
3,5-Dimethyl-4-[2-(3-nitro-phenylamino)-pyrimidin-4-yl]-1H-pyrrole-2-carbonitrile;
4-[2-(4-Fluoro-phenylamino)-pyrimidin-4-yl]-3,5-dimethyl-1H-pyrrole-2-carbonitrile;
4-[2-(4-Hydroxy-phenylamino)-pyrimidin-4-yl]-3,5-dimethyl-1H-pyrrole-2-carbonitrile;
3,5-Dimethyl-4-[2-(4-trifluoromethyl-phenylamino)-pyrimidin-4-yl]-1H-pyrrole-2-carbonitrile;
4-[2-(4-Iodo-phenylamino)-pyrimidin-4-yl]-3,5-dimethyl-1H-pyrrole-2-carbonitrile;
4-[2-(3-Hydroxy-phenylamino)-pyrimidin-4-yl]-3,5-dimethyl-1H-pyrrole-2-carbonitrile;
3,5-Dimethyl-4-[2-(4-methyl-3-nitro-phenylamino)-pyrimidin-4-yl]-1H-pyrrole-2-carbonitrile;
4-[2-(3-Hydroxy-4-methyl-phenylamino)-pyrimidin-4-yl]-3,5-dimethyl-1H-pyrrole-2-carbonitrile;
4-[2-(4-Fluoro-3-methyl-phenylamino)-pyrimidin-4-yl]-3,5-dimethyl-1H-pyrrole-2-carbonitrile;
4-[2-(4-Fluoro-phenylamino)-pyrimidin-4-yl]-3,5-dimethyl-1H-pyrrole-2-carboxylic acid amide;
[4-(2,4-Dimethyl-5-nitro-1H-pyrrol-3-yl)-pyrimidin-2-yl]-(4-fluoro-phenyl)-amine; 4-(5-Bromo-2,4-dimethyl-1H-pyrrol-3-yl)-pyrimidin-2-yl]-(3-nitro-phenyl)-amine, and [4-(5-Dimethylaminomethyl-2,4-dimethyl-1H-pyrrol-3-yl)-pyrimidin-2-yl]-(4-fluoro-phenyl)-amine.

19. A compound of general formula I:

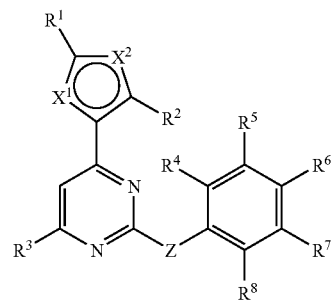

wherein:
one of $X^1$ and $X^2$ is $NR^{10}$ and the other of $X^1$ and $X^2$ is $CR^9$;
Z is NHCO, NHSO$_2$, NHCH$_2$, CH$_2$, CH$_2$CH$_2$, or CH=CH;
$R^1$, $R^2$, $R^3$ $R^9$ and $R^{10}$ are independently H, alkyl, aryl, aralkyl, heterocycle, halogeno, NO$_2$, CN, OH, alkoxy, aryloxy, (R''')nNH$_2$, (R''')$_n$NH—R', (R''')$_n$N—(R')(R"), NH-aryl, N-(aryl)$_2$, COOH, COO—R', COO-aryl, CONH$_2$, CONH—R', CON—(R')(R"), CONH-aryl, CON-(aryl)$_2$, SO$_3$H, SO$_2$NH$_2$, CF$_3$, CO—R', or CO-aryl, wherein alkyl, aryl, aralkyl and heterocycle groups may be further substituted with one or more groups selected from halogeno, NO$_2$, CN, OH, O-methyl, NH$_2$, COOH, CONH$_2$ and CF$_3$;
$R^4$, $R^5$, $R^6$, $R^7$, and $R^8$ are independently from each other H, substituted or unsubstituted lower alkyl, halogeno, NO$_2$, CN, OH, substituted or unsubstituted alkoxy, NH$_2$, NH—R', N—(R')(R"), COOH, COO—R', CONH$_2$, CONH—R', CON—(R')(R"), SO$_3$H, SO$_2$NH$_2$, or CF$_3$;
wherein R'R"and R''' are each independently alkyl groups that may be the same or different and n is 0 or 1, or a pharmaceutically acceptable salt thereof.

20. A compound of general formula I:

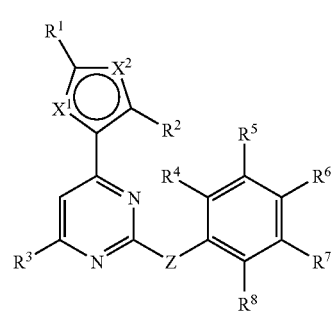

wherein:
$X^1$ is NH;
$X_2$ is $CR^9$;
Z is NH;
$R^1$, $R^2$, $R^3$ and $R^9$ are each independently selected from H, alkyl, aryl, aralkyl, heterocycle, halogeno, NO$_2$, CN, OH, alkoxy, aryloxy, (R''')$_n$NH$_2$, (R''')$_n$NH—R', (R''')$_n$ N—(R')(R"), COOH, COO—R', CONH$_2$, CONH—R', CON—(R')(R"), SO$_3$H, SO$_2$NH$_2$, CF$_3$, and CO—R' wherein alkyl, aryl and aralkyl groups may be further substituted with one or more groups selected from halogeno, NO$_2$, CN, OH, O-methyl, NH$_2$, COOH, CONH$_2$ and CF$_3$;

R$^4$, R$^5$ and R$^8$ are each independently selected from H, halogeno, nitro, amino, aminoalkyl, hydroxy, alkoxy, carbamoyl, sulfamyl, N(R')(R"), C$_{1-4}$ alkyl and substituted C$_{1-4}$ alkyl;

R$^6$ is selected from H, halogeno, nitro, amino, aminoalkyl, hydroxy, alkoxy, carbamoyl, sulfamyl, N(R')(R"), butyl and substituted C$_{1-4}$ alkyl;

R$^7$ is selected from H, halogeno, nitro, amino, aminoalkyl, hydroxy, carbamoyl, sulfamyl, N(R')(R") C$_{2-4}$ alkyl and substituted C$_{1-4}$ alkyl;

wherein R'R" and R'" are each independently alkyl groups that may be the same or different and n is 0 or 1, wherein at least two or three of R$^1$, R$^2$, and R$^9$ are not hydrogen, or a pharmaceutically acceptable salt thereof.

21. A compound according to claim 1 or 19, wherein R$^3$ is H.

22. A compound according to claim 21, wherein R$^1$, R$^2$ and R$^9$ are each independently H, halogeno, CN, NO$_2$, CO(NH$_2$), (R'")NH(R')(R") a C$_{1-4}$ alkyl group or a heterocyclic group.

23. A compound according to claim 22, wherein when R$^1$ is halogeno, it is selected from chloro or bromo; when R$^1$ is alkylamino, it is diethylaminomethyl or dimethylaminomethyl; when R$^1$ is a heterocyclic group it is morpholin-4-ylmethyl or 4-methyl-piperazin-1-ylmethyl.

24. A compound according to claim 1 or 19, wherein R is H or CN, and R$^2$ and R$^9$ are both methyl.

25. A compound according to claim 24, wherein R$^1$ is H.

26. A compound according to claim 25, wherein R$^1$ is CN.

27. A compound according to claim 1 or 19, wherein; R$^4$, R$^5$, R$^6$, R$^7$, and R$^8$ are independently from each other H, unsubstituted lower alkyl, halogeno, NO$_2$, CN, OH, N—(R')(R"), or CF$_3$;

wherein R'R" and R'" are each independently alkyl groups that may be the same or different and n is 0 or 1.

28. A compound according to claim 27, wherein R$^4$ to R$^8$ are selected independently from H, F, NH$_2$, NO$_2$, OH, Cl, Br, I, CN, CH$_2$OH, CF$_3$ and dimethylamino.

29. A compound according to claim 27, wherein R$^4$ and R$^8$ are both hydrogen.

30. A compound according to claim 19, wherein;

X$^1$ and X$^2$ are NH and CR$^9$ respectively;

Rhu 1, R$^2$, R$^3$ and R$^9$ are each independently selected from H, alkyl, aryl, aralkyl, heterocycle, halogene, NO$_2$, CN, OH, alkoxy, aryloxy, (R'")nNH$_2$,(R'")nNH—R', (R'")nN—(R')(R"), COOH, COO—R', CONH$_2$, CONH—R', CON—(R')(R"), SO$_3$H, SO$_2$NH$_2$, CF$_3$, and CO—R' wherein alkyl, aryl and aralkyl groups may be firther substituted with one or more groups selected from halogene, NO$_2$, CN, OH, O-methyyl, NH$_2$, COOH, CONH$_2$ and CF$_3$;

Z is selected from NHSO$_2$ and NHCH$_2$;

R$^4$, R$^5$ and R$^8$ are each independently selected from H, halogeno, nitro, amino, aminoalkyl, hydroxy, alkoxy, carbamoyl, sulfamyl, N(R')(R"), C$_{1-4}$ alkyl and substituted C$_{1-4}$ alkyl;

R6 is selected from H, halogeno, nitro, amino, aminoalkyl, hydroxy, alkoxy, carbamoyl, sulfamyl, N(R')(R"), methyl, propyl, butyl and substituted C$_{1-4}$ alkyl;

R7 is selected from H, halogeno, nitro, amino, aminoalkyl, hydroxy, carbamoyl, sulfamyl, N(R')(R"C$_{2-4}$ alkyl and substituted C$_{1-4}$ alkyl.

31. A pharmaceutical composition comprising a compound of claim 1 or a pharmaceutically acceptable salt thereof together with a pharmaceutically acceptable excipient.

32. A pharmaceutical composition comprising a compound of claim 19 or 20 or a pharmaceutical acceptable salt thereof together with a pharmaceutically acceptable excipient.

33. A method of treating a subject for a CDK dependent proliferative disorder, comprising administering to a subject a compound of claim 1 or a pharmaceutically acceptable salt thereof, such that said CDK dependent proliferative disorder in said subject is treated, wherein said CDK dependent proliferative disorder is lung cancer, cervical cancer, colon cancer, breast cancer, or bone cancer.

34. The method of claim 33, wherein said compound is administered in an amount sufficient to inhibit at least one CDK enzyme.

35. The method of claim 34, wherein the CDK enzyme is CDK2 andlor CDK4.

36. A method of treating a subject for a CDK dependent proliferative disorder, comprising administering to a subject a compound of claim 19 or 20 or a pharmaceutically acceptable salt thereof, such that said CDK dependent proliferative disorder in said subject is treated, wherein said CDK dependent proliferative disorder is lung cancer, cervical cancer, colon cancer, breast cancer, or bone cancer.

37. The method of claim 36, wherein said compound is administered in an amount sufficient to inhibit at least one CDK enzyme.

38. The method of claim 37, wherein the CDK enzyme is CDK2 and/or CDK4.

39. A method of treating a subject for lung cancer, cervical cancer, colon cancer, breast cancer, or bone cancer, comprising administering to a subject a compound of general formula 1 or a pharmaceutically acceptable salt thereof such that said lung cancer, cervical cancer, colon cancer, breast cancer, or bone cancer in said subject is treated, wherein said compound of general formula 1 is.

wherein:

one of X$^1$ and X$^2$ is NR$^{10}$ and the other of X$^1$ and X$^2$ is CR$^9$;

Z is NH, NHCO, NHSO$_2$, NHCH$_2$, CH$_2$, CH$_2$CH$_2$, or CH=CH;

R$^1$, R$^2$, R$^3$ R$^9$ and R$_{10}$ are independently H, alkyl, aryl, aralkyl, heterocycle, halogeno, NO$_2$, CN, OH, alkoxy, aryloxy, (R'")nNH$_2$, (R'")nNH—R', (R'")nN—(R')(R"), NH-aryl, N-(aryl)$_2$, COOH, COO—R', COO-aryl, CONH$_2$, CONH—R', CON—(R')(R"), CONH-aryl, CON-(aryl)$_2$, SO$_3$H, SO$_2$NH$_2$, CF$_3$, CO—R', or CO-aryl, wherein alkyl, aryl, aralkyl and heterocycle groups may be further substituted with one or more groups selected from halogeno, NO$_2$, CN, OH, O-methyl, NH$_2$, COOH, CONH$_2$ and CF$_3$;

R$^4$, R$^5$, R$^6$, R$^7$, and R$^8$ are independently from each other H, substituted or unsubstituted lower alkyl, halogeno, NO$_2$, CN, OH, substituted or unsubstituted alkoxy, NH$_2$, NH—R', N—(R')(R"), COOH, COO—R', CONH$_2$, CONH—R', CON—(R')(R"), SO$_3$H, SO$_2$NIH$_2$, or CF$_3$;

wherein R'R" and R'" are each independently alkyl groups that may be the same or different and n is 0 or 1, wherein at least two or three of R$^1$, R$^2$, and R$_9$ are not hydrogen; or a pharmaceutically acceptable salte thereof.

40. The method of claim 39, wherein said compound is administered in an amount sufficient to inhibit at least one CDK enzyme.

41. The method of claim 40, wherein the CDK enzyme is CDK2 and/or CDK4.

* * * * *